United States Patent
Chen et al.

(10) Patent No.: US 12,123,037 B2
(45) Date of Patent: Oct. 22, 2024

(54) LINOLEIC ACID ISOMERASE AND ITS APPLICATION IN PRODUCTION OF CONJUGATED LINOLEIC ACID

(71) Applicants: Haiqin Chen, Wuxi (CN); Bo Yang, Wuxi (CN); He Gao, Wuxi (CN); Jianxin Zhao, Wuxi (CN); Yongquan Chen, Wuxi (CN); Hao Zhang, Wuxi (CN); Wei Chen, Wuxi (CN)

(72) Inventors: Haiqin Chen, Wuxi (CN); Bo Yang, Wuxi (CN); He Gao, Wuxi (CN); Jianxin Zhao, Wuxi (CN); Yongquan Chen, Wuxi (CN); Hao Zhang, Wuxi (CN); Wei Chen, Wuxi (CN)

(73) Assignee: Jiangnan University, Wuxi (CN)

( * ) Notice: Subject to any disclaimer, the term of this patent is extended or adjusted under 35 U.S.C. 154(b) by 507 days.

(21) Appl. No.: 17/497,963

(22) Filed: Oct. 10, 2021

(65) Prior Publication Data
US 2022/0017886 A1     Jan. 20, 2022

Related U.S. Application Data

(63) Continuation of application No. PCT/CN2019/121822, filed on Nov. 29, 2019.

(30) Foreign Application Priority Data

| Oct. 23, 2019 | (CN) | .......................... 201911011728.3 |
| Oct. 25, 2019 | (CN) | .......................... 201911020755.7 |
| Oct. 25, 2019 | (CN) | .......................... 201911025170.4 |

(51) Int. Cl.
*C12N 9/90* (2006.01)
*C12P 7/6427* (2022.01)

(52) U.S. Cl.
CPC .............. *C12N 9/90* (2013.01); *C12P 7/6427* (2013.01); *C12Y 502/01005* (2013.01)

(58) Field of Classification Search
CPC ........ C12N 15/00; C12N 15/09; C12N 15/63; C12N 15/66; C12N 15/70; C12N 15/75
See application file for complete search history.

(56) References Cited

PUBLICATIONS

Mei et al. 2022. Heterologous expression of a novel linoleic acid isomerase BBI, and effect of fusion tags on its performance, Current Research in Food Science 5 (2022) 2053-2060. (Year: 2022).*

* cited by examiner

*Primary Examiner* — Tekchand Saidha
(74) *Attorney, Agent, or Firm* — Lili Chen

(57) ABSTRACT

Disclosed is linoleic acid isomerases and their application in production of conjugated linoleic acid, which belongs to the technical fields of protein engineering and microbial engineering. The linoleic acid isomerase derived from *Bifidobacterium* is used to produce the conjugated linoleic acid. The recombinant *E. coli* containing the linoleic acid isomerase of the invention is added into a reaction system containing linoleic acid and react for 3 h to produce conjugated linoleic acids. The conversion rate of the conjugated linoleic acid of the invented method ranges from 12.1% to 42.1%, and the percentage of cis9, trans11-CLA in the conjugated linoleic acid can reach 84.3% to 89.1%. The invention provides a method for using microorganisms to produce conjugated linoleic acids with high safety and yield where cis9, trans11-CLA isomer is the major form in the conjugated linoleic acid products.

18 Claims, 21 Drawing Sheets
Specification includes a Sequence Listing.

SEQUENCE LISTING

<160> NUMBER OF SEQ ID NOS: 18

<210> SEQ ID NO 1
<211> LENGTH: 330
<212> TYPE: PRT
<213> ORGANISM: Bifidobacterium breve

<400> SEQUENCE: 1

```
Met Leu Phe Gln Val Tyr Gly Asp Asn Ala Ile Tyr Gln Trp Ile Gly
1               5                   10                  15

Trp Ile Leu Val Phe Cys Cys Leu Ile Gly Ala Asn Glu Leu Ala Arg
            20                  25                  30

Arg Thr Lys Thr Gly Gly Ile Val Ala Phe Leu Val Val Pro Ala Val
        35                  40                  45

Leu Thr Val Tyr Phe Ile Thr Ile Tyr Thr Ala Ala Ala Met Gly Ala
    50                  55                  60

Asp Trp Ala Leu Asn Asn Pro Thr Tyr Val His Met Thr Ser Trp Phe
65                  70                  75                  80

His Tyr Ala Lys Leu Tyr Ala Ala Thr Ile Gly Cys Ile Gly Phe Met
                85                  90                  95
```

```
Ala Leu Lys Tyr Lys Trp Gly Ser Ile Gly Lys Ser His Trp Phe Lys
            100                 105                 110

Cys Phe Pro Phe Val Ile Val Ala Ile Asn Ile Leu Ile Ala Val Val
            115                 120                 125

Ser Asp Phe Glu Ser Ala Ile Arg Gly Trp Gly Thr Thr Trp Ile Ser
130                 135                 140

Thr Glu Gly Val Thr Leu Tyr Gly Gly Trp His Asn Val Phe Asn Gly
145                 150                 155                 160

Leu Ala Gly Ile Leu Asn Ile Phe Cys Met Thr Gly Trp Phe Gly Ile
                165                 170                 175

Tyr Ala Ser Lys Lys Asp Asp Met Leu Trp Pro Asp Met Thr Trp
            180                 185                 190

Val Phe Ile Val Ala Tyr Asp Leu Trp Asn Phe Cys Tyr Thr Tyr Asn
            195                 200                 205

Cys Leu Pro Thr His Ser Trp Tyr Cys Gly Leu Ala Leu Leu Leu Ala
            210                 215                 220

Pro Thr Val Ala Asn Phe Phe Trp Asn Lys Gly Gly Trp Ile Gln Asn
225                 230                 235                 240

Arg Ala Asn Thr Leu Ala Ile Trp Cys Met Phe Ala Gln Val Phe Pro
                245                 250                 255

Met Phe Gln Asp Tyr Ser Val Phe Ser Thr Gln Ser Val Asn Asn Pro
            260                 265                 270

Asn Val Asn Leu Ala Val Ser Leu Ile Ala Leu Val Ala Asn Val Leu
            275                 280                 285

Ala Leu Gly Tyr Ile Leu Leu Arg Ala Lys Lys Gln Gly Ile Asn Pro
            290                 295                 300

Trp Thr Lys Glu Val Phe Lys Gly Thr Lys Asp Tyr Glu Gln Ala Ile
305                 310                 315                 320

Ala Arg Ala Asp Ala Ser Glu Leu Val Ala
                325                 330

<210> SEQ ID NO 2
<211> LENGTH: 330
<212> TYPE: PRT
<213> ORGANISM: Bifidobacterium longum

<400> SEQUENCE: 2

Met Leu Phe Gln Val Tyr Gly Asp Asn Ala Ile Tyr Gln Trp Ile Gly
1               5                   10                  15

Trp Ile Leu Val Phe Cys Cys Leu Ile Gly Ala Asn Glu Leu Ala Arg
            20                  25                  30

Arg Thr Lys Thr Gly Gly Val Ile Ala Phe Leu Val Ile Pro Ala Val
            35                  40                  45

Leu Thr Val Tyr Phe Ile Thr Ile Tyr Thr Ala Ala Met Gly Ala
            50                  55                  60

Asp Trp Ala Leu Asn Asn Pro Thr Tyr Val His Met Thr Ser Trp Phe
65                  70                  75                  80

His Tyr Ala Lys Leu Tyr Ala Ala Thr Ile Gly Cys Ile Gly Phe Met
                85                  90                  95

Ala Leu Lys Tyr Lys Trp Gly Ser Ile Gly Lys Ser His Trp Phe Lys
            100                 105                 110

Cys Phe Pro Phe Val Ile Val Ala Ile Asn Ile Leu Ile Ala Val Val
            115                 120                 125

Ser Asp Phe Glu Ser Ala Ile Arg Gly Trp Gly Thr Thr Trp Ile Ser
130                 135                 140
```

```
Thr Glu Gly Val Thr Leu Tyr Gly Gly Trp His Asn Val Phe Asn Gly
145                 150                 155                 160

Val Ala Gly Leu Leu Asn Ile Phe Cys Met Thr Gly Trp Phe Gly Ile
                165                 170                 175

Tyr Ala Ser Lys Lys Asp Asp Met Leu Trp Pro Asp Met Thr Trp
            180                 185                 190

Val Phe Ile Val Ala Tyr Asp Leu Trp Asn Phe Cys Tyr Thr Tyr Asn
            195                 200                 205

Cys Leu Pro Thr His Ala Trp Tyr Cys Gly Leu Ala Leu Leu Ala
            210                 215                 220

Pro Thr Val Ala Asn Phe Phe Trp Asn Lys Gly Gly Trp Ile Gln Asn
225                 230                 235                 240

Arg Ala Asn Thr Leu Ala Ile Trp Cys Met Phe Ala Gln Val Phe Pro
                245                 250                 255

Met Phe Gln Asp Tyr Ser Met Phe Ser Thr Gln Ser Val Asn Asn Pro
            260                 265                 270

Asn Val Asn Leu Ala Val Ser Leu Ile Ala Leu Ala Ala Asn Val Leu
            275                 280                 285

Ala Leu Gly Tyr Ile Leu Leu Arg Ala Lys Lys Gln Gly Ile Asn Pro
            290                 295                 300

Trp Thr Lys Glu Val Phe Lys Gly Thr Lys Asp Tyr Glu Gln Ala Ile
305                 310                 315                 320

Ala Arg Ala Asp Glu Ser Glu Leu Ala Ala
            325                 330

<210> SEQ ID NO 3
<211> LENGTH: 327
<212> TYPE: PRT
<213> ORGANISM: Bifidobacterium pseudocatenulatum

<400> SEQUENCE: 3

Met Leu Phe Gln Val Tyr Gly Asp Thr Ala Ile Tyr Gln Trp Ile Gly
1               5                   10                  15

Trp Ile Leu Val Phe Cys Cys Leu Ile Gly Ala Asn Glu Leu Ala Arg
                20                  25                  30

Arg Thr Lys Thr Gly Gly Val Ile Ala Phe Leu Ile Val Pro Ala Ile
            35                  40                  45

Leu Thr Ile Tyr Phe Ile Thr Ile Tyr Val Ala Ala Ala Met Gly Ala
            50                  55                  60

Glu Trp Ala Leu Ser Asn Pro Thr Tyr Val His Met Thr Ser Trp Phe
65                  70                  75                  80

His Tyr Ala Lys Leu Tyr Ala Ala Thr Ala Gly Cys Ile Gly Phe Met
                85                  90                  95

Ala Leu Lys Tyr Lys Trp Gly Lys Ile Gly Lys Ser Glu Trp Phe Lys
                100                 105                 110

Cys Phe Pro Phe Val Ile Val Ala Ile Asn Ile Leu Ile Ala Val Ala
            115                 120                 125

Ser Asp Phe Glu Ser Ala Ile Arg Ala Trp Gly Thr Thr Trp Val Ser
            130                 135                 140

Thr Glu Gly Val Thr Leu Tyr Gly Gly Trp His Asn Val Phe Asn Gly
145                 150                 155                 160

Val Ala Gly Leu Ile Asn Ile Ala Cys Met Thr Gly Trp Phe Gly Ile
                165                 170                 175

Tyr Val Ser Lys Lys Lys Gln Asp Met Leu Trp Pro Asp Met Thr Trp
```

```
            180                 185                 190
Val Phe Ile Val Ala Tyr Asp Ile Trp Asn Phe Cys Tyr Thr Tyr Asn
            195                 200                 205

Cys Leu Pro Thr His Ser Trp Tyr Cys Gly Leu Ala Leu Leu Leu Ala
        210                 215                 220

Pro Thr Val Ala Asn Phe Phe Trp Asn Lys Gly Trp Ile Gln Asn
225                 230                 235                 240

Arg Ala Asn Thr Leu Ala Ile Trp Cys Met Phe Ala Gln Val Phe Pro
                245                 250                 255

Met Phe Gln Asp Glu Ser Lys Phe Ala Val Gln Ser Val Asn Asn Pro
                260                 265                 270

Asn Val Asn Leu Thr Val Ser Ile Ile Ala Leu Val Ala Asn Val Leu
        275                 280                 285

Ala Leu Gly Tyr Ile Met Tyr Arg Ala Lys Lys Gln His Val Asn Pro
            290                 295                 300

Trp Leu Gln Glu Val Phe Lys Gly Thr Arg Asp Tyr Glu Gln Ala Ile
305                 310                 315                 320

Ala Arg Gln Glu Val Ala Ala
                325

<210> SEQ ID NO 4
<211> LENGTH: 328
<212> TYPE: PRT
<213> ORGANISM: Bifidobacterium dentium

<400> SEQUENCE: 4

Met Leu Phe Gln Val Tyr Gly Asp Thr Ala Val Tyr Gln Trp Ile Gly
1               5                   10                  15

Trp Ile Leu Val Phe Cys Cys Leu Ile Gly Ala Asn Glu Leu Ala Arg
            20                  25                  30

Arg Thr Lys Thr Gly Gly Ile Val Ala Phe Leu Val Val Pro Ala Ile
            35                  40                  45

Leu Thr Val Tyr Phe Ile Thr Ile Tyr Val Ala Ala Ala Gly Ala
        50                  55                  60

Glu Trp Ala Leu Thr Asn Pro Thr Tyr Val His Met Thr Ser Trp Phe
65                  70                  75                  80

His Tyr Ala Lys Leu Tyr Ala Ala Thr Ala Gly Cys Ile Gly Phe Met
                85                  90                  95

Ala Leu Lys Tyr Lys Trp Gly Ala Ile Gly Lys Ser Glu Trp Phe Lys
            100                 105                 110

Cys Phe Pro Phe Val Ile Val Ala Ile Asn Ile Leu Ile Ala Val Val
        115                 120                 125

Ser Asp Phe Glu Ser Ala Ile Arg Ala Trp Gly Thr Thr Trp Val Ser
        130                 135                 140

Thr Glu Gly Val Thr Leu Met Gly Gly Trp His Asn Val Phe Asn Gly
145                 150                 155                 160

Val Ala Gly Leu Ile Asn Ile Ala Cys Met Thr Gly Trp Phe Gly Ile
                165                 170                 175

Tyr Val Ser Lys Arg Lys Gln Asp Met Leu Trp Pro Asp Met Thr Trp
            180                 185                 190

Val Phe Ile Val Ala Tyr Asp Leu Trp Asn Phe Cys Tyr Thr Tyr Asn
            195                 200                 205

Cys Leu Pro Thr His Ser Trp Tyr Cys Gly Leu Ala Leu Leu Leu Ala
        210                 215                 220
```

```
Pro Thr Val Ala Asn Phe Phe Trp Asn Lys Gly Gly Trp Ile Gln Asn
225                 230                 235                 240

Arg Ala Asn Thr Leu Ala Ile Trp Cys Met Phe Ala Gln Val Phe Pro
            245                 250                 255

Ala Phe Gln Asp Glu Ser Lys Phe Ala Val Gln Ser Val Asn Asn Pro
        260                 265                 270

Asn Val Asn Leu Thr Val Ser Ile Ile Ala Leu Val Ala Asn Val Leu
    275                 280                 285

Ala Phe Gly Tyr Ile Met Tyr Arg Ala Arg Lys Gln His Val Asn Pro
    290                 295                 300

Trp Leu Gln Glu Val Phe Thr Gly Thr Lys Asp Phe Glu Gln Ala Met
305                 310                 315                 320

Ala Arg Arg Glu Asp Leu Ala Ala
                325
```

<210> SEQ ID NO 5
<211> LENGTH: 993
<212> TYPE: DNA
<213> ORGANISM: Bifidobacterium breve

<400> SEQUENCE: 5

```
atgctgtttc aggtctacgg cgacaacgcc atctaccaat ggattggctg gatactcgtc     60
ttctgctgcc ttatcggcgc caatgaactg gctcgtcgca ccaaaaccgg cggcatcgtc    120
gccttcctcg tcgtcccggc tgtgctgacc gtctacttca tcaccatcta caccgccgcc    180
gcaatgggcg ccgactgggc actcaacaac ccgacctacg tgcacatgac cagctggttc    240
cactacgcca agctctacgc ggccaccatc ggctgcatcg gctttatggc cctcaaatac    300
aagtggggct ctatcggcaa atcccactgg ttcaagtgct ccccgttcgt gatcgtggcc    360
atcaacatcc tcatcgccgt ggtctctgac ttcgaatccg ccatccgcgg ctggggcacc    420
acctggatct ccactgaagg cgtgacccte tacggtggct ggcacaacgt gttcaacggc    480
ttggccggca tcctcaatat cttctgcatg accggctggt tcggcatcta cgcctccaag    540
aagaaggacg acatgctctg gccggacatg acctgggtgt catcgtggcc ctacgatctg    600
tggaacttct gctacaccta caattgcctg cccacccact cctggtactg cggccttgca    660
ctgctgctgg cgcccaccgt ggccaacttc ttctggaaca agggcggctg gatccagaat    720
cgcgccaata cattggccat ctggtgcatg ttcgcgcagg tattcccgat gttccaggac    780
tactccgtgt ctccacccca gtccgtgaac aacccgaacg tgaaccttgc ggtgtcccta    840
atcgcgctag tggccaacgt gttggcactc ggctacatcc tgctgcgcgc caagaagcag    900
ggcatcaacc cgtggaccaa ggaagtcttc aagggcacca agactacga gcaggccatc    960
gctcgcgccg atgcatcgga gttggtggcg tag                                 993
```

<210> SEQ ID NO 6
<211> LENGTH: 993
<212> TYPE: DNA
<213> ORGANISM: Bifidobacterium longum

<400> SEQUENCE: 6

```
atgctgtttc aggtctacgg cgacaacgcc atctaccaat ggatcggatg gatactcgtc     60
ttctgctgtc ttatcggcgc caacgaactg gcccgccgca ccaaaaccgg tggcgttatc    120
gccttcctcg tcataccggc cgtgctgacc gtctacttca tcaccatcta caccgccgcc    180
gccatgggtg ccgactgggc cctcaacaac ccgacctacg tacacatgac cagctggttc    240
```

| | | |
|---|---|---|
| cactatgcca agctgtacgc ggccaccatc ggctgcatcg gtttcatggc cctcaaatac | 300 | |
| aagtggggat ccatcggcaa atcgcactgg ttcaagtgct tcccgttcgt gatcgtggcc | 360 | |
| atcaacatcc tcattgccgt agtgtccgac ttcgaatccg ccatccgcgg ctggggcacc | 420 | |
| acgtggatct ccaccgaagg cgtgaccctg tacggtggcg gcacaacgt cttcaacggc | 480 | |
| gtggccggcc tgctcaacat cttctgcatg accggctggt tcggcatcta cgcctccaag | 540 | |
| aagaaggacg acatgctctg gccggacatg acctgggtgt tcatcgtggc ctacgacctg | 600 | |
| tggaacttct gctacaccta caactgcctg cccacccacg cctggtattg cggcctggcg | 660 | |
| ctgctgctgg cacccaccgt ggccaacttc ttctggaaca agggcggttg gattcagaac | 720 | |
| cgcgccaaca cgctggccat ctggtgcatg ttcgcgcagg tgttcccgat gttccaggac | 780 | |
| tattccatgt tctccaccca gtccgtgaac aatccgaatg tgaaccttgc agtctcgtta | 840 | |
| atcgcgttgg cggccaatgt gctggcactt ggctacatcc tgctacgcgc caagaagcag | 900 | |
| ggcatcaacc cgtggaccaa ggaagtgttc aaaggcacca aggattacga gcaggccatc | 960 | |
| gctcgcgccg acgagtctga attggcggcc tag | 993 | |

<210> SEQ ID NO 7
<211> LENGTH: 984
<212> TYPE: DNA
<213> ORGANISM: Bifidobacterium pseudocatenulatum

<400> SEQUENCE: 7

| | | |
|---|---|---|
| atgttgttcc aagtctatgg cgacaccgcc atataccagt ggatcggatg gatcctcgta | 60 | |
| ttctgctgcc tgatcggcgc caatgagctg gcccgtcgca ccaagaccgg tggcgtgatc | 120 | |
| gcgttcctga tcgtgccggc cattctgacc atctacttca tcaccattta cgtggccgcc | 180 | |
| gcgatgggtg ccgaatgggc gctcagcaat ccgacctacg tgcatatgac cagctggttc | 240 | |
| cactatgcca agctatatgc ggccaccgca ggctgcatcg gcttcatggc actcaaatac | 300 | |
| aagtggggca agatcggcaa atccgaatgg ttcaagtgct tcccgttcgt gatcgtggcc | 360 | |
| atcaacattc ttatcgccgt ggcctccgac ttcgaatcgg ccattcgcgc ttggggcacc | 420 | |
| acatgggttt ccaccgaagg cgtgacgctg tatggcggct ggcacaatgt gttcaacggc | 480 | |
| gttgccggcc tgatcaacat cgcctgcatg accggctggt tcggcattta cgtgtcaaag | 540 | |
| aagaagcaag acatgctgtg gcctgacatg acttgggtat tcatcgtcgc atacgatatt | 600 | |
| tggaacttct gctacaccta caactgcctg ccgacccact cctggtattg cggcctcgcg | 660 | |
| ctgctgctcg ccccgaccgt ggcgaacttc ttctggaaca agggcggctg gatcagaaac | 720 | |
| cgcgccaaca cgctcgccat ctggtgcatg ttcgcgcagg tgttccccat gttccaggat | 780 | |
| gagtccaagt tcgccgtgca gtcggtgaac aatccgaacg tgaacctgac cgtgtcgatc | 840 | |
| atcgcgctcg tggccaacgt gctcgcactc ggctacatca tgtaccgcgc gaagaagcag | 900 | |
| cacgtcaacc cgtggctgca ggaagtcttc aagggcaccc gcgactacga gcaggccatc | 960 | |
| gcccgccagg aagtcgccgc ctga | 984 | |

<210> SEQ ID NO 8
<211> LENGTH: 986
<212> TYPE: DNA
<213> ORGANISM: Bifidobacterium dentium

<400> SEQUENCE: 8

| | | |
|---|---|---|
| atgttgttcc aagtctatgg cgacaccgcc gtatatcagt ggatcggctg gatccttgtc | 60 | |
| ttctgctgcc tgatcggcgc caatgagctg gcccgccgca ccaagaccgg cggtatcgtg | 120 | |

```
gcgttcctgg tcgttcctgc gatcctgacc gtctatttca tcaccatcta tgtagccgct    180
gccgccggcg ccgaatgggc gctgaccaac ccgacctacg tgcacatgac cagctggttc    240
cattatgcga aactgtacgc agcgaccgcg ggatgcatcg gcttcatggc actcaagtac    300
aagtggggcg ccatcggcaa atccgaatgg ttcaaatgct ccccgttcgt aatcgtggcc    360
atcaacatcc tcatcgccgt ggtttccgac ttcgaatccg cgatccgcgc atggggcacc    420
acctgggtct ccaccgaagg cgtgacgctc atgggcggct ggcacaacgt gttcaacggc    480
gtggcgggcc tcatcaacat cgcctgcatg accggatggt tcggcatcta cgtgtcgaag    540
aggaagcagg acatgctctg gcccgacatg acgtgggtgt tcatcgtagc ctacgacctg    600
tggaacttct gctacaccta caactgcctg cccacccact cgtggtactg cggtctggcg    660
ctgctgcttg caccgaccgt cgccaacttc ttctggaaca agggcggctg gattcagaac    720
cgcgccaaca cactcgccat ctggtgcatg ttcgcgcagg tgttccctgc cttccaggac    780
gagtccaagt tcgccgtgca gtcggtgaac aacccgaacg tgaacctgac cgtgtcgatc    840
atcgcactcg tggcgaacgt gctcgcattc ggctatatca tgtaccgtgc caggaagcag    900
cacgtgaacc cgtggctgca ggaggtgttc acggcaccaa ggactttgag caggccatgg    960
cccgccgcga agatctggcg gcctga    986

<210> SEQ ID NO 9
<211> LENGTH: 29
<212> TYPE: DNA
<213> ORGANISM: Artificial sequence
<220> FEATURE:
<223> OTHER INFORMATION: Synthetic DNA sequence

<400> SEQUENCE: 9
aagcctatgc tgtttcaggt ctacggcga                                       29

<210> SEQ ID NO 10
<211> LENGTH: 25
<212> TYPE: DNA
<213> ORGANISM: Artificial sequence
<220> FEATURE:
<223> OTHER INFORMATION: Synthetic DNA sequence

<400> SEQUENCE: 10
catatgctac gccaccaact ccgat                                           25

<210> SEQ ID NO 11
<211> LENGTH: 25
<212> TYPE: DNA
<213> ORGANISM: Artificial sequence
<220> FEATURE:
<223> OTHER INFORMATION: Synthetic DNA sequence

<400> SEQUENCE: 11
aagcctatgc tgtttcaggt ctacg                                           25

<210> SEQ ID NO 12
<211> LENGTH: 25
<212> TYPE: DNA
<213> ORGANISM: Artificial sequence
<220> FEATURE:
<223> OTHER INFORMATION: Synthetic DNA sequence

<400> SEQUENCE: 12
catatgctag gccgccaatt cagac                                           25
```

<210> SEQ ID NO 13
<211> LENGTH: 25
<212> TYPE: DNA
<213> ORGANISM: Artificial sequence
<220> FEATURE:
<223> OTHER INFORMATION: Synthetic DNA sequence

<400> SEQUENCE: 13
aagcctatgt tgttccaagt ctatg                                    25

<210> SEQ ID NO 14
<211> LENGTH: 25
<212> TYPE: DNA
<213> ORGANISM: Artificial sequence
<220> FEATURE:
<223> OTHER INFORMATION: Synthetic DNA sequence

<400> SEQUENCE: 14
catatgtcag gcggcgactt cctgg                                    25

<210> SEQ ID NO 15
<211> LENGTH: 25
<212> TYPE: DNA
<213> ORGANISM: Artificial sequence
<220> FEATURE:
<223> OTHER INFORMATION: Synthetic DNA sequence

<400> SEQUENCE: 15
aagcctatgt tgttccaagt ctatg                                    25

<210> SEQ ID NO 16
<211> LENGTH: 25
<212> TYPE: DNA
<213> ORGANISM: Artificial sequence
<220> FEATURE:
<223> OTHER INFORMATION: Synthetic DNA sequence

<400> SEQUENCE: 16
catatgtcag gccgccagat cttcg                                    25

<210> SEQ ID NO 17
<211> LENGTH: 1005
<212> TYPE: DNA
<213> ORGANISM: Artificial sequence
<220> FEATURE:
<223> OTHER INFORMATION: Synthetic DNA sequence

<400> SEQUENCE: 17
ggatccatgc tgttccaggt gtacggagac aacgccatct accagtggat tggttggatt      60
ctggtcttct gttgcctgat cggtgctaac gagctggctc gacgaaccaa gaccggcgga     120
attgtggcct tcctggtggt ccccgctgtg ctgaccgtct acttcatcac catctacacc     180
gctgctgcta tgggagctga ctgggctctg aacaacccca cctacgtgca catgaccctc     240
tggttccact acgccaagct gtacgctgcc accattggtt gtatcggctt catggctctg     300
aagtacaagt ggggctctat tggcaagtct cactggttca agtgcttccc cttcgtgatc     360
gtcgccatca acattctgat cgctgtggtc tccgacttcg agtctgccat tcgaggctgg     420
ggaaccacct ggatctccac cgagggagtg accctgtacg gtggctggca acgtcttc      480 aacggcctgg ccggaattct gaacatcttc tgtatgaccg gttggttcgg catctacgct     540
tctaagaaga aggacgacat gctgtggccc gacatgacct gggtgttcat tgtcgcctac     600
gacctgtgga acttctgtta cacctacaac tgcctgccca cccactcctg gtactgtggt     660

```
ctggctctgc tgctggctcc taccgtggct aacttcttct ggaacaaggg aggttggatt        720
cagaaccgag ccaacaccct ggctatctgg tgcatgttcg cccaggtctt ccccatgttc        780
caggactact ctgtgttctc cacccagtct gtcaacaacc ccaacgtgaa cctggctgtc        840
tctctgattg ctctggtggc taacgtcctg gctctgggct acattctgct gcgagctaag        900
aagcagggaa tcaacccctg gaccaaggaa gtgttcaagg gcaccaagga ctacgagcag        960
gctattgctc gagctgacgc ttctgagctg gtggcttagg gtacc                       1005

<210> SEQ ID NO 18
<211> LENGTH: 993
<212> TYPE: DNA
<213> ORGANISM: Artificial sequence
<220> FEATURE:
<223> OTHER INFORMATION: Synthetic DNA sequence

<400> SEQUENCE: 18 atgcttttc aagtctatgg tgacaatgct atatatcaat ggattggatg gattttagtc         60
ttttgttgtc ttattggagc taatgaactt gcaagaagaa caaaaacagg aggaattgtt        120 gcattttag ttgttccagc tgttttaact gtttattta ttaccatata taccgccgca         180
gctatgggag cagattggc tttaaataat ccaacttatg ttcatatgac ctcatggttt        240
cattatgcta aattatatgc cgcaacaatt ggatgtattg gttttatggc tttaaaatat        300
aaatggggaa gcattggaaa atcacattgg tttaaatgtt ttccatttgt cattgtcgct        360
attaatattc ttattgctgt cgtttctgat tttgaatctg caattcgtgg ttggggaaca        420
acttggattt caactgaagg agttacatta tatggtggtt ggcataatgt tttaatgga         480 ttagctggaa ttttgaatat tttctgtatg actggatggt ttggaatata tgcatcaaaa        540
aagaaagatg atatgctttg gcctgatatg acatgggttt ttattgttgc atatgatctt        600 tggaatttt gttataccta taattgtctt ccaacccatt cttggtattg tggtttagct        660
ttattacttg ctcctacagt tgctaatttc ttttggaata agggtggatg gattcaaaat        720
agagcaaata ctttagctat ttggtgtatg tttgctcaag tttttcctat gtttcaagat        780
tatagcgttt ttagtaccca atcagttaat aatcctaatg ttaatcttgc cgtttcatta        840
attgctttag ttgctaatgt ccttgcatta ggatatattt tacttagagc aaaaaagcaa        900
ggtattaatc catggacaaa agaagttttt aaaggtacaa aagattatga acaagccatt        960
gctcgtgctg atgcttcaga attagttgca taa                                    993
```

LINOLEIC ACID ISOMERASE AND ITS APPLICATION IN PRODUCTION OF CONJUGATED LINOLEIC ACID

CROSS-REFERENCES AND RELATED APPLICATIONS

This application is a continuation of international application PCT/CN2019/121822, filed Nov. 29, 2019, which claims the benefit of priority to Chinese patent application No. 2019110207557, filed Oct. 25, 2019, and Chinese patent application No. 2019110117283, filed Oct. 23, 2019, and Chinese patent application No. 2019110251704, filed Oct. 25, 2019, the content of which are hereby incorporated by reference in the entirety.

BACKGROUND OF THE INVENTION

Field of the Invention

The present invention relates to a linoleic acid isomerase and its application in production of conjugated linoleic acid, which belongs to the technical fields of protein engineering and microbial engineering.

Description of the Related Art

Conjugated linoleic acid (CLA) is a general term for a series of fatty acids with conjugated double bonds and various positional and geometric isomers. Studies have shown that the conjugated linoleic acid has the physiological effects of anti-cancer, lowering lipids, regulating metabolism, enhancing immunity and promoting growth and development, and is widely used in the fields of medicines, foods, cosmetics, etc. Moreover, cis9, trans11-CLA, and trans10, cis12-CLA are the two isomers with the most physiological activities among conjugated linoleic acid isomers. Therefore, there are huge demands for cis9, trans11-CLA, and trans10, cis12-CLA on the market.

Natural conjugated linoleic acids mainly exist in rumen animals, some plants and marine organisms, and the natural conjugated linoleic acids mainly exist in the form of cis9, trans11-CLA, with extremely high physiological activity. However, the amount of natural linoleic acid is very small, which can hardly meet the market demand for the conjugated linoleic acids. Therefore, people have developed methods for synthesizing conjugated linoleic acids.

At present, the methods for synthesizing the conjugated linoleic acid include chemical and microbial synthesis methods. The chemical synthesis method will lead to production of many toxic by-products which poison the environment and human bodies. Conjugated linoleic acid prepared by the chemical synthesis method contains many types of isomers, of which the effective separation is quite difficult/Therefore the chemical synthesis method cannot achieve large-scale industrial production of the conjugated linoleic acid. Compared with the chemical synthesis method, the microbial synthesis method causes less pollution and can obtain conjugated linoleic acid in a single form of the isomers. Therefore, the microbial synthesis method is a method having high potential to achieve large-scale industrial production of the conjugated linoleic acid.

However, the existing microbial synthesis method has the following defects:

First, most microorganisms capable of achieving the high yield of conjugated linoleic acid such as *Butyrivibrio fibrisolvens*, *Propionibacterium* and *Clostridium sporogenes* are pathogenic bacteria which have great safety issues and cannot be directly used as strains for industrial production of conjugated linoleic acid.

Second, some microorganisms capable of achieving the high yield of conjugated linoleic acid such as *Lactobacillus plantarum* ZS2058 (Qi Hui, Yang Bo et al., Molecular Mechanism of Conjugated Linoleic Acid Synthesis in *Lactobacillus plantarum* ZS2058 [D], Jiangnan University, 2017) has too low yield for producing conjugated linoleic acid to be used in industrial production.

Third, most microorganisms capable of achieving the high yield of conjugated linoleic acid such as *Butyrivibrio fibrisolvens* and *Bifidobacterium* are strict anaerobes that are not easy to be cultured industrially or in a laboratory and have a low yield, which can hardly be applied in the field of foods and medicines.

Fourth, some CLA production strains such as *Lactobacillus plantarum* ZS2058 (Qi Hui, Yang Bo et al., Molecular Mechanism of Conjugated Linoleic Acid Synthesis in *Lactobacillus Plantarum* ZS2058 [D], Jiangnan University, 2017) strictly relies on linoleic acid as a substrate. High concentration of free linoleic acid and by-products will inhibit the growth of CLA bacteria, thereby affecting their conversion rates and leading to low production efficiency.

All of the above defects make the existing microbial synthesis method unable to achieve the large-scale industrial production of the conjugated linoleic acid. Therefore, there is an urgent need to find a conjugated linoleic acid production strain not being strictly anaerobic, high in safety, not strictly dependent on linoleic acid as a substrate and high in production yield.

SUMMARY OF THE INVENTION

The present invention provides a recombinant cell carrying a recombinant plasmid, which comprises a gene encoding the linoleic acid isomerase (EC 5.2.1.5), and nucleotide sequences of the linoleic acid isomerase gene are set forth in SEQ ID NO: 5, 6, 7, 8, 17 and 18. Alternatively, the linoleic acid isomerase is derived from *Bifidobacterium breve*, with an amino acid sequence set forth in SEQ ID NO: 1; alternatively, the linoleic acid isomerase is derived from *Bifidobacterium longum*, with an amino acid sequence set forth in SEQ ID NO: 2; alternatively, the linoleic acid isomerase is derived from *Bifidobacterium pseudocatenulatum*, with an amino acid sequence set forth in SEQ ID NO: 3; alternatively, the linoleic acid isomerase is derived from *Bifidobacterium dentium*, with an amino acid sequence set forth in SEQ ID NO: 4.

In an embodiment of the invention, the recombinant cell is *E. coli*, *Yarrowia lipolytica* or *Lactobacillus plantarum*.

In an embodiment of the invention, the vector of the recombinant plasmid is a pET-28a(+) plasmid, a pINA 1312sp plasmid or a pNZ44 plasmid.

In an embodiment of the invention, the recombinant cell is *E. coli* that carries a gene for encoding a linoleic acid isomerase in pET-28a(+) plasmid, with the nucleotide sequences of the linoleic gene set forth in SEQ ID NO: 5, 6, 7 and 8.

In an embodiment of the invention, the recombinant cell is *Yarrowia lipolytica* that carries a gene encoding the linoleic acid isomerase in the pINA 1312sp plasmid, with the nucleotide sequence of the linoleic gene set forth in SEQ ID NO: 17.

In an embodiment of the invention, the recombinant cell is *Lactobacillus plantarum* that carries a gene encoding the linoleic acid isomerase in the pNZ44 plasmid, with the nucleotide sequence of the linoleic gene set forth in SEQ ID NO: 18.

In an embodiment of the invention, it provides a method for producing conjugated linoleic acid using the recombinant cell that carries the linoleic acid isomerase gene.

In an embodiment of the invention, it provides a method for producing conjugated linoleic acid using the recombinant *E. coli* cells. The method includes the following steps: inoculating a culture medium with the above recombinant cell, and performing culturing at 35° C. to 40° C. and at a rotating speed of 150 to 250 rpm until $OD_{600}$ is 0.4 to 0.6 to obtain a culture solution A; adding IPTG with a final concentration of 0.01 to 1.0 mM into the culture solution A, and performing induction at 15° C. to 20° C. with a rotating speed of 150 to 250 rpm for 12 to 16 h to obtain a culture solution B; centrifuging the culture solution B and collecting wet bacterial cells; adding the wet bacterial cells into a reaction system containing linoleic acid, and performing the reaction at 35° C. to 40° C. with a rotating speed of 150 to 250 rpm to obtain a reaction solution rich in conjugated linoleic acid; and extracting the reaction solution rich in conjugated linoleic acid to obtain the conjugated linoleic acid.

In an embodiment of the invention, it provides a method for producing conjugated linoleic acid using the recombinant *Yarrowia lipolytica* cells. The method includes the following steps: inoculating a culture medium containing linoleic acid and/or glyceride with the above recombinant cell, and performing culturing at 35° C. to 40° C. with a rotating speed of 150 to 250 rpm to obtain a recombinant cell rich in conjugated linoleic acid, and then extracting the recombinant cell rich in conjugated linoleic acid to obtain the conjugated linoleic acid.

In an embodiment of the invention, it provides a method for producing conjugated linoleic acid using the recombinant *Lactobacillus plantarum* cells. The method includes the following steps: inoculating a culture medium containing linoleic acid with the above recombinant cell, and performing stationary culturing at 37° C. to obtain a culture solution rich in conjugated linoleic acid; and extracting the culture solution rich in conjugated linoleic acid to obtain the conjugated linoleic acid.

In an embodiment of the invention, it provides a method for producing conjugated linoleic acid using the recombinant *E. coli* cells. The method includes the following steps: inoculating a culture medium with the above recombinant cell, and performing culturing at 37° C. with a rotating speed of 200 rpm until $OD_{600}$ is 0.4 to 0.6 to obtain a culture solution A; adding IPTG with a final concentration of 0.01 to 1.0 mM into the culture solution A, and performing induction culture at 18° C. with a rotating speed of 200 rpm for 12 to 16 h to obtain a culture solution B; centrifuging the culture solution B, and collecting wet bacterial cells; adding the wet bacterial cells into a reaction system containing linoleic acid, and performing reaction at 37° C. and at a rotating speed of 200 rpm to obtain reaction solution rich in conjugated linoleic acid; and extracting the reaction solution rich in conjugated linoleic acid to obtain the conjugated linoleic acid.

In an embodiment of the invention, the recombinant cell is *Yarrowia lipolytica* and the glyceride is safflower oil, linseed oil, cottonseed oil, and/or soybean oil.

In an embodiment of the invention, the recombinant cell is *Yarrowia lipolytica* and the glyceride is safflower oil.

In an embodiment of the invention, the recombinant cell is *E. coli* and the reaction system contains a buffer solution and the linoleic acid.

In an embodiment of the invention, the recombinant cell is *E. coli* and the buffer solution has a pH of 6 to 7.

In an embodiment of the invention, the recombinant cell is *E. coli* and the buffer solution has a pH of 6.5.

In an embodiment of the invention, the recombinant cell is *E. coli* and the buffer solution is a potassium phosphate buffer solution.

In an embodiment of the invention, the recombinant cell is *E. coli* and the linoleic acid in the reaction system has a concentration of 0.05 to 0.15 mg/mL.

In an embodiment of the invention, the recombinant cell is *E. coli* and the linoleic acid in the reaction system has a concentration of 0.1 mg/mL.

In an embodiment of the invention, the recombinant cell is *E. coli* and the wet bacterial cells in the reaction system have a concentration of 0.5 to 2 mg/mL.

In an embodiment of the invention, the recombinant cell is *E. coli* and the wet bacterial cells in the reaction system have a concentration of 1 mg/mL.

In an embodiment of the invention, the recombinant cell is *E. coli* and the conjugated linoleic acid is cis9, trans11-CLA and/or trans9, trans11-CLA.

In an embodiment of the invention, the recombinant cell is *Yarrowia lipolytica* and the conjugated linoleic acid is cis9, trans11-CLA, trans10, cis12-CLA and/or trans9, trans11-CLA.

In an embodiment of the invention, the recombinant cell is *Lactobacillus plantarum* and the conjugated linoleic acid is cis9, trans11-CLA.

In an embodiment of the invention, the recombinant cell is *E. coli*, *Yarrowia lipolytica* or *Lactobacillus plantarum*, and the conjugated linoleic acid is cis9, trans11-CLA.

In an embodiment of the invention, the recombinant cell is *E. coli* and the culture medium is an LB culture medium.

In an embodiment of the invention, the recombinant cell is *Yarrowia lipolytica* and the culture medium is a YPD culture medium.

In an embodiment of the invention, the recombinant cell is *Lactobacillus plantarum* and the culture medium is an MRS culture medium.

In an embodiment of the invention, it provides a method of using the recombinant cell to produce linoleic acid isomerase. The linoleic acid isomerase has an amino acid sequence set forth in SEQ ID NO: 1.

In an embodiment of the invention, the recombinant *E. coli* cells are used to produce linoleic acid isomerase. The method includes the following steps: adding the recombinant *E. coli*. cells into a culture medium and culture at 35° C. to 40° C. with a rotating speed of 150 to 250 rpm, to obtain a recombinant cell rich in linoleic acid isomerase, and then extracting the recombinant cell rich in linoleic acid isomerase to obtain the linoleic acid isomerase.

In an embodiment of the invention, the recombinant *Yarrowia lipolytica* cells are used to produce linoleic acid isomerase. The method includes the following steps: inoculating a culture medium with the recombinant cells, performing the culture at 35° C. to 40° C. with a rotating speed of 150 to 250 rpm, to obtain recombinant cells rich in linoleic acid isomerase, and then extracting the recombinant cell rich in linoleic acid isomerase to obtain the linoleic acid isomerase.

In an embodiment of the invention, the recombinant *Lactobacillus plantarum* cells are used to produce linoleic acid isomerase. The method includes the following steps:

inoculating a culture medium with the above recombinant cells, performing a stationary culture at 37° C. to obtain recombinant cells rich in linoleic acid isomerase, and then extracting the recombinant cells rich in linoleic acid isomerase to obtain the linoleic acid isomerase.

In an embodiment of the invention, the recombinant cell is *E. coli* and the culture medium is an LB culture medium.

In an embodiment of the invention, the recombinant cell is *Yarrowia lipolytica* and the culture medium is a YPD culture medium.

In an embodiment of the invention, the recombinant cell is *Lactobacillus plantarum* and the culture medium is an MRS culture medium.

Beneficial Effects:

(1) The invention provides a method to use recombinant *E. coli* comprising the linoleic acid isomerase of *Bifidobacterium breve* with the amino acid sequence of SEQ ID NO: 1 to produce the conjugated linoleic acid. The recombinant *E. coli* containing the linoleic acid isomerase are added into the reaction system with the linoleic acid to react for 3 h. The conversion rate of the conjugated linoleic acid can reach up to 42.1%, and the content of cis9, trans11-CLA in the conjugated linoleic acid can reach up to 89.1%. The invention provides a method for using safe recombinant microorganisms to produce conjugated linoleic acid monomers with the majority in the form of cis9, trans11-CLA.

(2) The invention provides a method to use recombinant *E. coli* comprising the linoleic acid isomerase of *Bifidobacterium longum* with the amino acid sequence of SEQ ID NO: 2 to produce the conjugated linoleic acid. The recombinant *E. coli* containing the linoleic acid isomerase of the invention are added into the reaction system containing the linoleic acid to react for 3 h. The conversion rate of the conjugated linoleic acid can reach up to 12.1%, and the amount of cis9, trans11-CLA in the conjugated linoleic acid can reach up to 84.3%.

(3) The invention provides a method to use recombinant *E. coli* comprising the linoleic acid isomerase of *Bifidobacterium pseudocatenulatum* with the amino acid sequence of SEQ ID NO: 3 to produce the conjugated linoleic acid. The recombinant *E. coli* containing the linoleic acid isomerase of the invention are added into the reaction system containing the linoleic acid to react for 3 h, then the conversion rate of the conjugated linoleic acid can reach up to 19.5%, the content of cis9, trans11-CLA in the conjugated linoleic acid can reach up to 88.9%.

(4) The invention provides a method to use recombinant *E. coli* comprising the linoleic acid isomerase of *Bifidobacterium dentium* with the amino acid sequence of SEQ ID NO: 4 to produce the conjugated linoleic acid. The recombinant *E. coli* containing the linoleic acid isomerase of the invention are added into the reaction system containing the linoleic acid to react for 3 h. The conversion rate of the conjugated linoleic acid can reach up to 13.5% and the amount of cis9, trans11-CLA in the conjugated linoleic acid can reach up to 87.15%.

(5) The present invention provides a method of using recombinant *Yarrowia lipolytica* to produce high-yield conjugated linoleic acid in which the glyceride such as the safflower oil is used as a substrate. The method of the invention can increase the percentage of cis9, trans11-CLA isomer in the conjugated linoleic acid product. The recombinant *Yarrowia lipolytica* strain of the invention is added into a culture medium containing free linoleic acid and is cultured for 36 h. The yield of the conjugated linoleic acid in fermentation broth can reach up to 5.8 mg/L, wherein the yield of cis9, trans11-CLA reaches up to 1.5 mg/L, which accounts for about 25% of the yield of the total conjugated linoleic acid. The recombinant *Yarrowia lipolytica* strain of the invention is added into a culture medium containing the safflower oil and is cultured for 36 h. The yield of the conjugated linoleic acid in fermentation broth can reach up to 751.7 mg/L, wherein the yield of cis9, trans11-CLA reaches up to 224.0 mg/L, which accounts for about 29.8% of the yield of the total conjugated linoleic acid.

(6) *Yarrowia lipolytica* is generally regarded as safe (GRAS) microorganism and has been identified as a safe strain capable of being used in foods by the EU. The conjugated linoleic acid produced by the recombinant *Yarrowia lipolytica* strain of the invention is relatively safe.

(7) *Yarrowia lipolytica* is a strictly aerobe and can be industrially cultured more easily compared with strictly anaerobes, and the industrial production process using *Yarrowia lipolytica* as a production strain has been very mature, so that the recombinant *Yarrowia lipolytica* strain of the invention is more suitable for large-scale industrial production.

(8) The glyceride such as the safflower oil is abundant in source and low in price, the recombinant *Yarrowia lipolytica* strain of the invention can be used to produce the conjugated linoleic acid with a high yield using the glyceride such as safflower oil as the substrate. Most conjugated linoleic acid isomers produced by the strain are cis9, trans11-CLA, The method of the invention for linoleic acid production is low in cost and suitable for large-scale industrial production.

(9) An engineered *Lactobacillus plantarum* strain of the invention can be used to produce the conjugated linoleic acid with a high yield. Most conjugated linoleic acid isomers produced by the strain are cis9, trans11-CLA. The *Lactobacillus plantarum* engineered strain of the invention is added into a culture medium containing linoleic acid and is cultured for 72 h. The conversion rate of the conjugated linoleic acid can reach up to 89.9%, and the percentage of cis9, trans11-CLA in the conjugated linoleic acid can reach up to 100%.

(10) *Lactobacillus plantarum* is a kind of probiotics, and has been listed in the List of Strains for Foods issued by the Ministry of Health at present. The conjugated linoleic acid produced by the *Lactobacillus plantarum* engineered strain of the invention is thus safe to human bodies.

(11) *Lactobacillus plantarum* belongs to a facultative aerobe, is easier to culture compared with strict anaerobes, and is suitable for large-scale industrial production.

DETAILED DESCRIPTION

Figure 1:
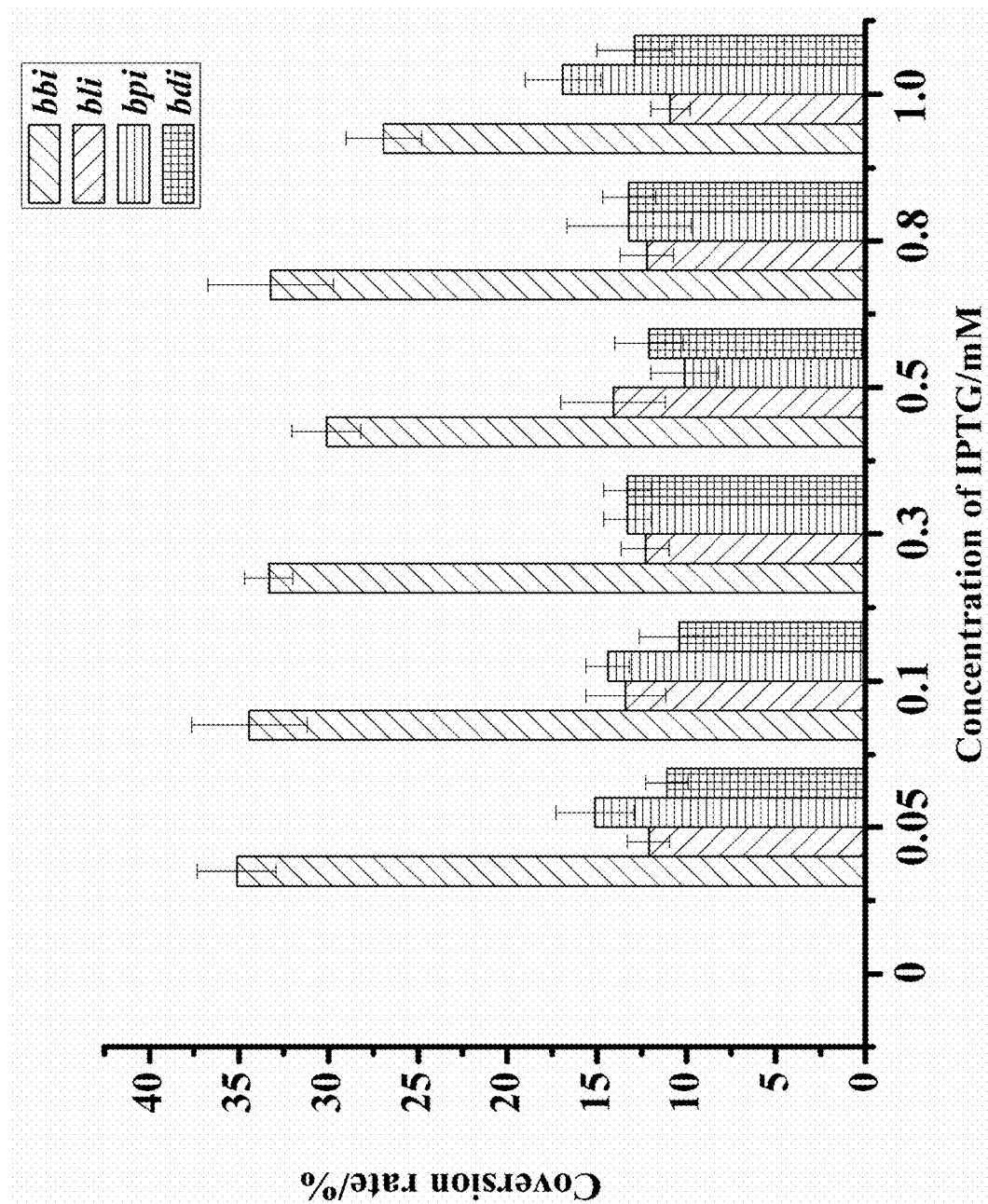
FIG. 1: Effects of concentration of IPTG on the conversion rate of conjugated linoleic acid produced by recombinant *E. coli* BL21 (DE3)/pET28a-bbi, *E. coli* BL21 (DE3)/pET28a-b/i, *E. coli* BL21 (DE3)/pET28a-bpi and *E. coli* BL21 (DE3)/pET28a-bdi.
Figure 2:
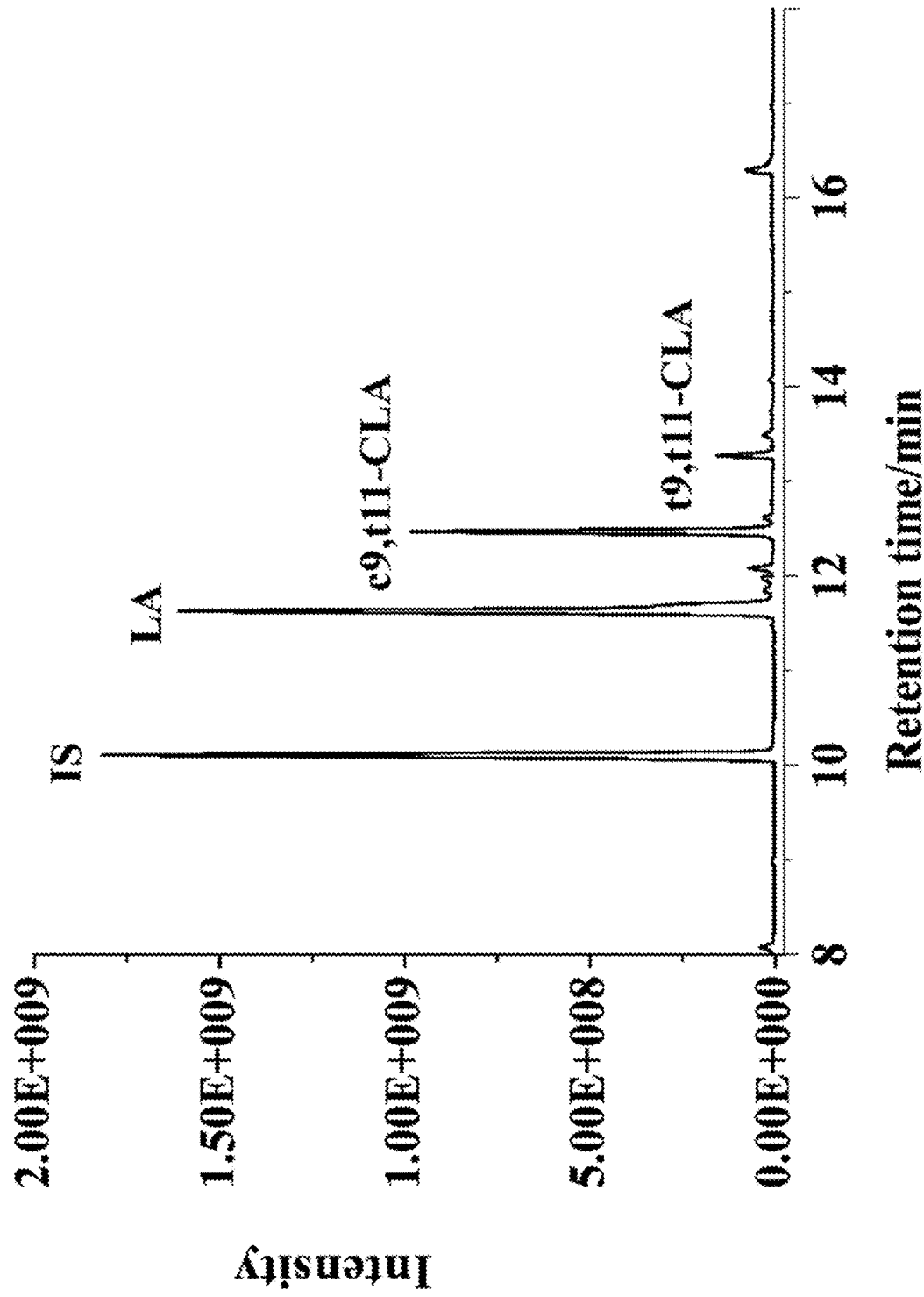
FIG. 2: Types and ratios of conjugated linoleic acid isomers in conjugated linoleic acid produced by recombinant *E. coli* BL21 (DE3)/pET28a-bbi.
Figure 3:
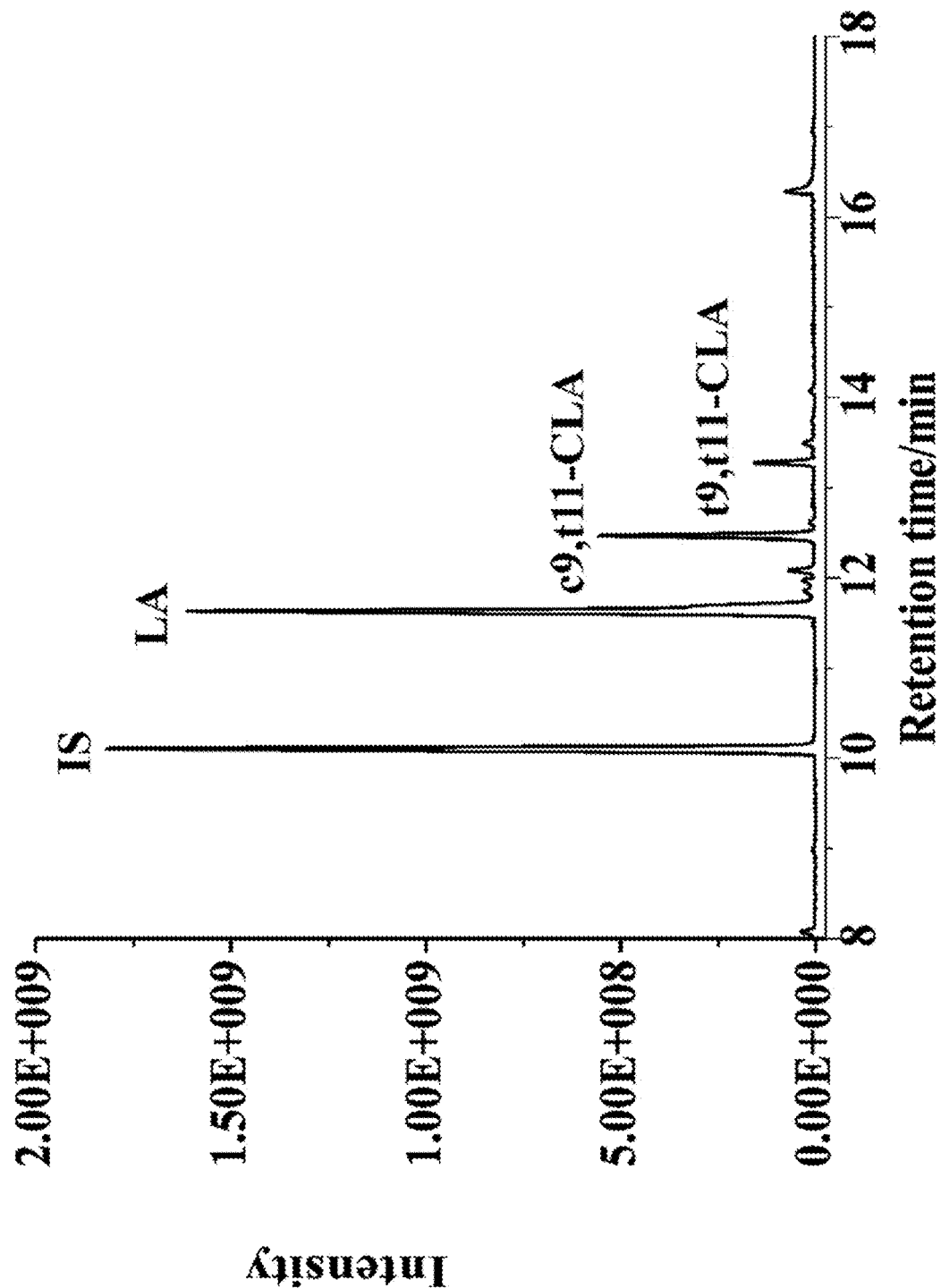
FIG. 3: Types and ratios of conjugated linoleic acid isomers in conjugated linoleic acid produced by recombinant *E. coli* BL21 (DE3)/pET28a-bli.
Figure 4:
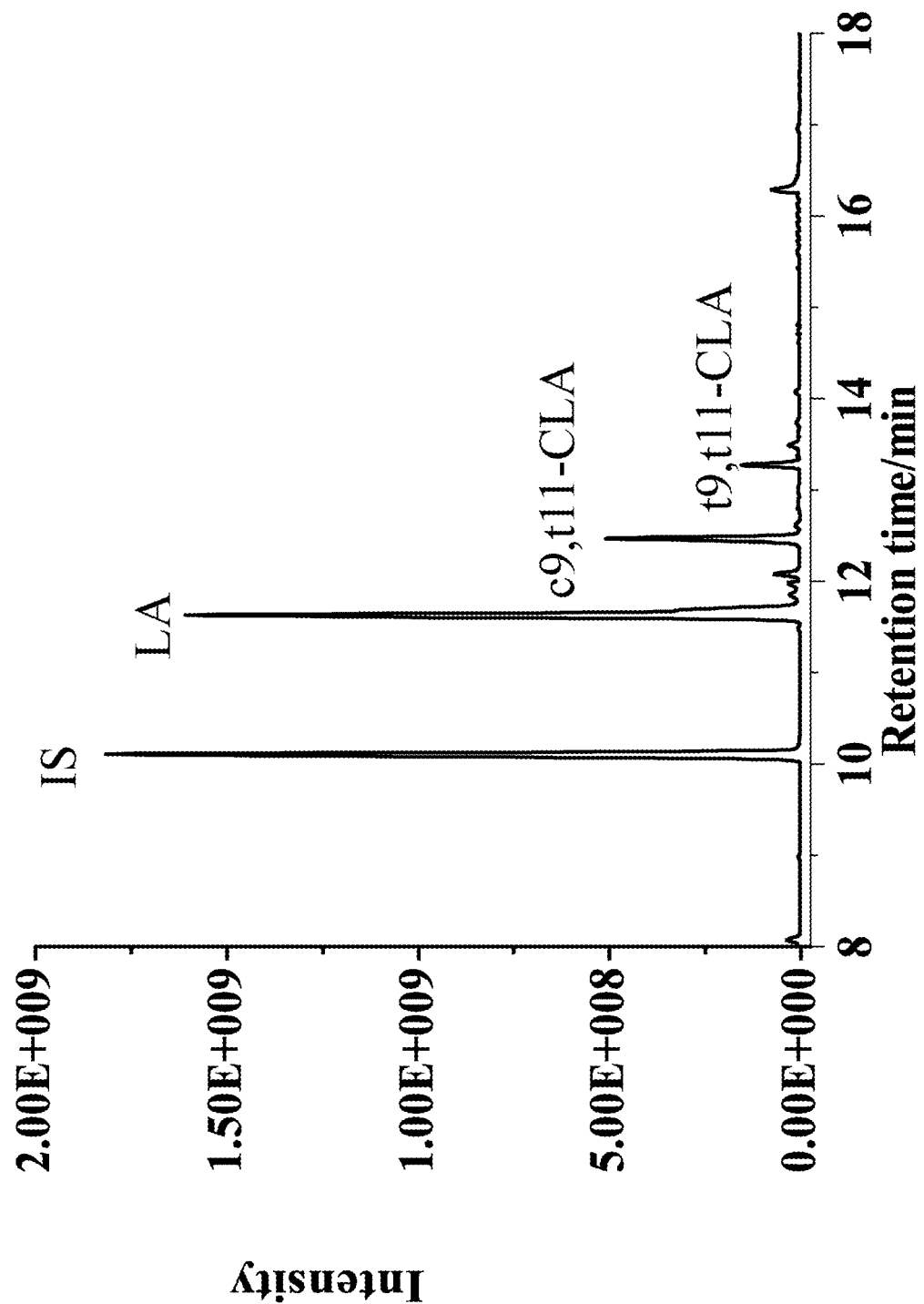
FIG. 4: Types and ratios of conjugated linoleic acid isomers in conjugated linoleic acid produced by recombinant *E. coli* BL21 (DE3)/pET28a-bpi.
Figure 5:
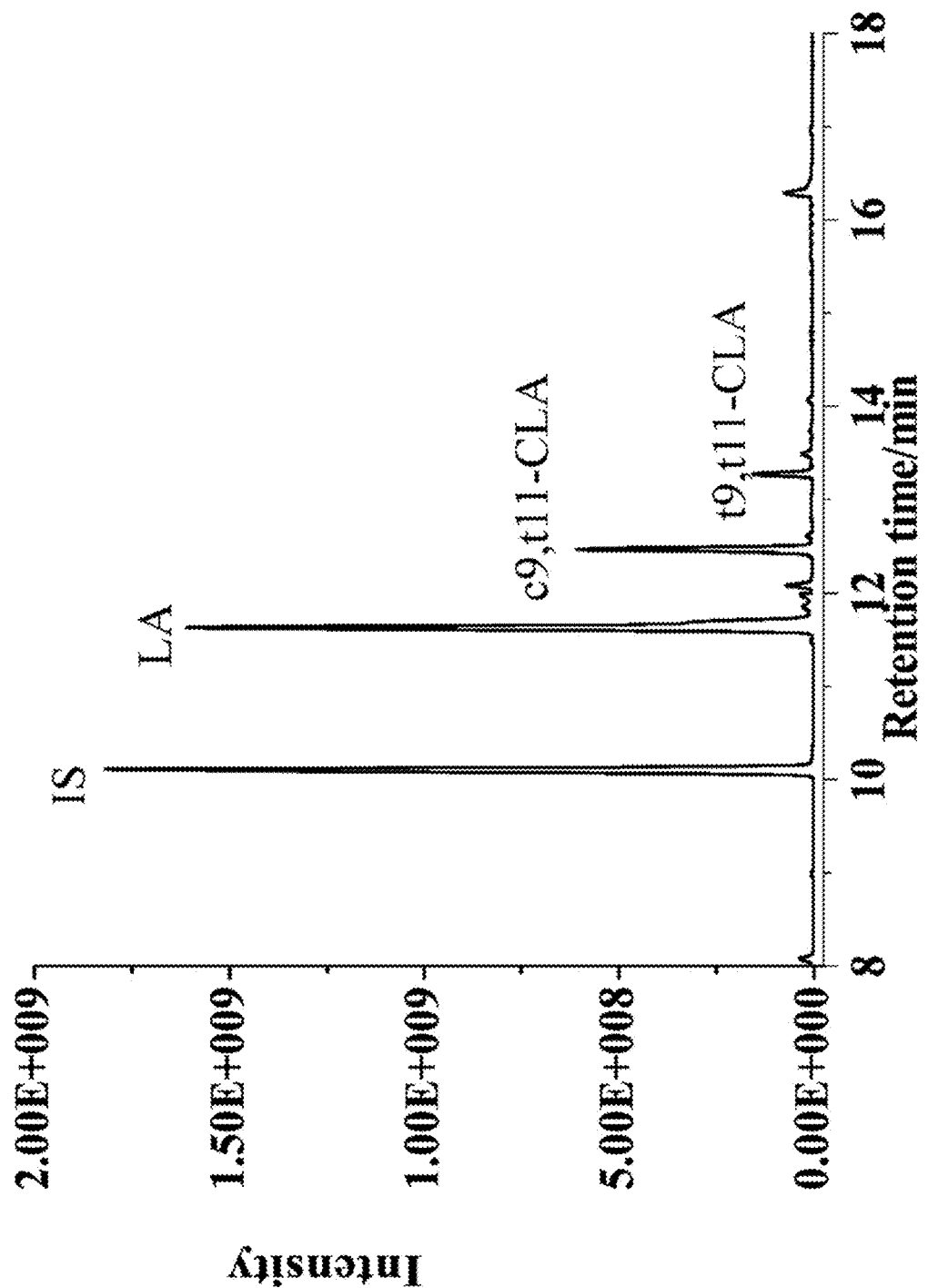
FIG. 5: Types and ratios of conjugated linoleic acid isomers in conjugated linoleic acid produced by recombinant *E. coli* BL21 (DE3)/pET28a-bdi.

Materials: Escherichia coli DH5a and E. coli BL21 (DE3) were purchased from GE. A pET-28a(+) vector was purchased from Invitrogen. A bacterial genome DNA extracting kit and a plasmid miniprep kit were purchased from Tiangen Biotech (Beijing) Co., Ltd. with model numbers being DP302 and DP103 respectively. Free linoleic acid was purchased from Sigma. Safflower oil was purchased from COFCO (Changji) Grain and Oil Industry Co., Ltd. Yarrowia lipolytica was purchased from BeNa Culture Collection, with the product number being BNCC193899. A pINA 1312 plasmid was purchased from BioVector NTCC. A construction method for a pINA 1312sp plasmid was reported in the literature "Zhang B, Chen H, Li M, Gu Z, Song Y, Ratledge C, Chen Y Q, Zhang H, Chen W (2013) Genetic engineering of Yarrowia lipolytica for enhanced production of trans-10, cis-12 conjugated linoleic acid. Microb Cell Fact. 12: 70". A construction method of a pNZ44 plasmid was reported in the literature "McGrath, S. et al., 2001. Improvement and optimization of two engineered phage resistance mechanisms in Lactobacoccus lactic. Applied and Environmental Microbiology, 67(2): 608-616."

Culture media involved in the following examples are as follows:

An MRS solid culture medium: Peptone 10 g/L, beef extract 10 g/L, glucose 20 g/L, sodium acetate 2 g/L, yeast powder 5 g/L, diammonium hydrogen citrate 2 g/L, $K_2HPO_4·3H_2O$ 2.6 g/L, $MgSO_4·7H_2O$ 0.1 g/L, $MnSO_4·H_2O$ 0.05 g/L, tween-80 1 mL/L, agar 15 g/L, and cysteine hydrochloride 0.5 g/L.

An MRS liquid culture medium: Peptone 10 g/L, beef extract 10 g/L, glucose 20 g/L, sodium acetate 2 g/L, yeast powder 5 g/L, diammonium hydrogen citrate 2 g/L, $K_2HPO_4·3H_2O$ 2.6 g/L, $MgSO_4·7H_2O$ 0.1 g/L, $MnSO_4·H_2O$ 0.05 g/L, tween-80 1 mL/L, and cysteine hydrochloride 0.5 g/L.

An LB liquid culture medium: Tryptone 10 g/L, yeast extract 5 g/L, and sodium chloride 10 g/L; and 100 μg/mL kanamycin is added before use.

An LB solid culture medium: Tryptone 10 g/L, yeast extract 5 g/L, sodium chloride 10 g/L, and agar 15 g/L; and 100 μg/mL kanamycin is added before use.

A YNBD solid culture medium: Yeast nitrogen base (no amino acid contained) 6.7 g/L, glucose 20 g/L, and agar 15 g/L; and pH is 5.5.

A YNBD liquid culture medium: Yeast nitrogen base (no amino acid contained) 6.7 g/L, and glucose 20 g/L; and pH is 5.5.

A YPD culture medium: Peptone 20 g/L, yeast extract 10 g/L, and glucose 20 g/L; and pH is 6.5.

Detection methods involved in the following examples are as follows:

A method for measuring the specific enzyme activity of linoleic acid isomerase: bacterial cells are collected and added into a KPB (pH 6.5), and the bacterial cells are crushed by glass beads to obtain a cell disruption solution; the cell disruption solution is centrifuged at 8000 g for 10 min, a supernatant is collected, and a crude enzyme is obtained; the protein content in the crude enzyme is adjusted to be 0.5 mg/mL, and the adjusted crude enzyme is separately loaded into 6 reaction glass bottles, 1 mL for each glass bottle; linoleic acid with a final concentration of 0.1 mg/mL is added into each glass bottle to react at 37° C. for 60 min, so as to obtain reaction solution; and after reaction is finished, isopropanol and n-hexane are quickly added into the reaction solution to extract fatty acid, and content change of the fatty acid is measured (for a detection method of the content change of the fatty acid, reference is made to a following detection method of a conversion rate of conjugated linoleic acid, and types and ratios of conjugated linoleic acid isomers in the conjugated linoleic acid), so that the specific enzyme activity is calculated. The specific enzyme activity (U/mg)=W/(T×M), where W is mass (μg) of conjugated linoleic acid generated by the reaction, T is reaction time (min), and M is mass (mg) of a sample to be tested.

The definition of the specific enzyme activity of the linoleic acid isomerase is the quantity of enzymes required by generating 1 mg of conjugated linoleic acid in a converting manner within 1 min under the conditions of 37° C. and pH 6.5, the unit being U/mg.

A method for measuring a conversion rate of conjugated linoleic acid in reaction solution, and types and ratios of conjugated linoleic acid isomers in the conjugated linoleic acid: According to a proportion of 1 mL of reaction solution+1 mL of isopropanol+2 mL of n-hexane, the isopropanol and the n-hexane are added into the reaction solution to obtain mixed solution; the mixed solution is subjected to vortex oscillation for 30 s; standing is performed for layering; an n-hexane layer at the upper layer is removed into a clean spiral glass bottle, and nitrogen is blown till dryness; then 400 μL of methanol is added, and vortex oscillation is performed for 30 s; 40 μL of diazomethane is added into each glass bottle for methyl esterification, a solution is yellow green at the moment, reaction is performed for 15 min, and if the color is not faded, it shows that methyl esterification is relatively sufficient; and solution after sufficient methyl esterification is dried through nitrogen blowing, 200 μL of n-hexane is added respectively for re-dissolution, and after centrifuging, a supernatant is transferred into a chromatographic sample injection bottle, and is temporarily stored until GC-MS detection.

The conversion rate of conjugated linoleic acid=(mass of conjugated linoleic acid/mass of linoleic acid in a control group)×100%.

A detection method of a yield of conjugated linoleic acid in cells, a yield of each conjugated linoleic acid isomer, a conversion rate of the conjugated linoleic acid, a conversion rate of each conjugated linoleic acid isomer, types of the conjugated linoleic acid isomers in the conjugated linoleic acid and ratios of the conjugated linoleic acid isomers: Fatty acid in recombinant *Yarrowia lipolytica* bacterial cells is subjected to methyl esterification by using a hydrochloric acid-methanol method: 20 to 25 mg of lyophilized bacterial powder is weighed, and placed in a 5 mL glass bottle, 100 μL of a C17:0 fatty acid internal standard substance (2.000 g/L) and 1 mL of 10% hydrochloric acid-methanol are added, and water bathing at 60° C. is performed for 3 h (1 min of oscillation every 30 min); after cooling to room temperature, 1 mL of n-hexane and 1 mL of saturated NaCl are added and oscillated to be evenly mixed, centrifuging at 3000×g is performed for 3 min, and a solution at the upper layer is sucked; and 1 mL of n-hexane is added into the original system and oscillated to be evenly mixed, centrifuging at 3000 g is performed for 3 min, a solution at the upper layer is sucked and combined, after nitrogen blow-drying, 1 mL of n-hexane is added and evenly mixed, and the mixture is transferred into a gas phase bottle for gas chromatography. A fatty acid analysis method refers to the literature "Yang Bo, Chen Haiqin, Song Yuanda, et al. Study of the Enzymatic Function of Myosin Cross Reactive Antigen from *Bifidobacterium animalis* [J]. China Biotechnology, 2012, 32(12): 30-36."

The yield of conjugated linoleic acid=(peak area of conjugated linoleic acid/internal standard peak area)×0.1 mL×2.0 mg/mL.

The yield of each conjugated linoleic acid isomer=(peak area of each conjugated linoleic acid isomer/internal standard peak area)×0.1 mL×2.0 mg/mL.

The conversion rate of conjugated linoleic acid=(mass of conjugated linoleic acid/mass of linoleic acid in a control group)×100%.

The conversion rate of each conjugated linoleic acid isomer=(mass of each conjugated linoleic acid isomer/mass of linoleic acid in a control group)×100%.

Example 1. Screening of Genes for Coding Linoleic Acid Isomerase

Transcriptomics data of *Bifidobacterium breve* CGMCC NO. 11828 (recorded in the text of the patent application with the publication number of CN105925514A) under stress of linoleic acid were collected through a PacBio sequencing platform, wherein sampling time points were the $3^{rd}$ h, $8^{th}$ h and $15^{th}$ h respectively. It was found through bioinformatic analysis that there were totally 8 genes with the gene transcription levels increased in the *Bifidobacterium breve* CGMCC NO. 11828 at the three time points, these 8 genes were respectively noted as the genes for coding "unknown protein 1", "melibiose carrier protein", "ribokinase", "linoleic acid hydratase", "unknown protein 2", "transcriptional control protein", "ribose-binding ABC channel protein 1" and "ribose-binding ABC channel protein 2" according to the change amplitude of the transcription level, wherein the transcription level of the gene for coding the "unknown protein 1" at the 8th h was increased by 68 times than that at the 3rd h, the transcription levels at the 15th h and the 8th h were up-regulated by 3.5 times and 8.2 times than that at the 3rd h, the gene did not form a gene cluster with other genes, and thus it was speculated that the gene had a relatively large possibility of participating in CLA conversion (an amino acid sequence of the "unknown protein 1" is shown in SEQ ID NO: 1, and a nucleotide sequence of the gene for coding the "unknown protein 1" is shown in SEQ ID NO: 5).

By means of the same method, other genes that may participate in CLA conversion were obtained from *Bifidobacterium longum, Bifidobacterium pseudocatenulatum* and *Bifidobacterium dentium* respectively (the genes which were obtained from *Bifidobacterium longum, Bifidobacterium pseudocatenulatum* and *Bifidobacterium dentium* respectively and might participate in CLA conversion were respectively noted as genes for coding "unknown protein 3", "unknown protein 4" and "unknown protein 5", wherein an amino acid sequence of the "unknown protein 3" is shown in SEQ ID NO: 2, a nucleotide sequence of the gene for coding the "unknown protein 3" is shown in SEQ ID NO: 6, an amino acid sequence of the "unknown protein 4" is shown in SEQ ID NO: 3, a nucleotide sequence of the gene for coding the "unknown protein 4" is shown in SEQ ID NO: 7, an amino acid sequence of the "unknown protein 5" is shown in SEQ ID NO: 4, and a nucleotide sequence of the gene for coding the "unknown protein 5" is shown in SEQ ID NO: 8).

Example 2. Cloning of Genes for Coding Linoleic Acid Isomerase

A bacterial solution of *Bifidobacterium breve* CGMCC NO. 11828 was picked from a bacteria storing tube, streaked on an MRS solid culture medium and was cultured in a 37° C. constant-temperature anaerobic chamber for 48 h, so as to obtain a single colony; the single colony was picked, an MRS liquid culture medium was inoculated with the single colony, stationary culturing was continued in the 37° C. constant-temperature anaerobic chamber for 24 h, and activation continued for 3 generations to obtain an activated bacterial solution; an MRS liquid culture medium was inoculated with the activated bacterial solution according to the inoculation quantity of 1% (v/v), and culturing was performed in the 37° C. constant-temperature anaerobic chamber for 24 h, so as to obtain a bacterial suspension; the obtained bacterial suspension was centrifuged under the conditions of 25° C. and 12000 g for 10 min to obtain wet bacterial cells; genome DNA in the wet bacterial cells was extracted by using a bacterial genome DNA extracting kit, and bbi was amplified through PCR; an amplified product was obtained after the PCR was finished, the size of a stripe of the amplified product was verified through 1% agarose gel electrophoresis after the amplified product was purified, and bbi (this bbi gene was the gene for coding the "unknown protein 1") was obtained, wherein primers for amplifying bbi are shown in Table 1.

A PCR system contains: KOD 1 µL, ddH$_2$O 29 µL, upstream primers 1 µL, downstream primers 1 µL, genome DNA 1 µL, dNTP 5 µL, 10× reaction buffer 5 µL and Mg$^{2+}$ 3 µL.

PCR conditions are: 95° C., 5 min; cycling (95° C., 30 s; 55° C., 30 s; 68° C., 1 min) 30 times; 68° C., 5 min; and 12° C., 5 min.

By means of the same method for obtaining bbi, bli (this bli gene was the gene for coding "unknown protein 3"), bpi (this bpi gene was the gene for coding "unknown protein 4") and bdi (this bdi gene was the gene for coding "unknown protein 5") were obtained from *Bifidobacterium longum*, *Bifidobacterium pseudocatenulatum* and *Bifidobacterium dentium* respectively, wherein primers for amplifying bli, bpi and bdi are shown in Table 1.

TABLE 1

Primer Sequences

| Primer name | | Primers (5'-3') |
|---|---|---|
| bbi | F | SEQ ID NO: 9:<br>AAGCCTATGCTGTTTCAGGTCTACGGCGA |
|  | R | SEQ ID NO: 10:<br>CATATGCTACGCCACCAACTCCGAT |
| bli | F | SEQ ID NO: 11:<br>AAGCCTATGCTGTTTCAGGTCTACG |
|  | R | SEQ ID NO: 12:<br>CATATGCTAGGCCGCCAATTCAGAC |
| bpi | F | SEQ ID NO: 13:<br>AAGCCTATGTTGTTCCAAGTCTATG |
|  | R | SEQ ID NO: 14:<br>CATATGTCAGGCGGCGACTTCCTGG |
| bdi | F | SEQ ID NO: 15:<br>AAGCCTATGTTGTTCCAAGTCTATG |
|  | R | SEQ ID NO: 16:<br>CATATGTCAGGCCGCCAGATCTTCG |

Example 3. Expression of Linoleic Acid Isomerase in *E. coli*

A pET-28a(+) vector was guided into *E. coli* DH5a to obtain *E. coli* DH5a/pET28a; the *E. coli* DH5a/pET28a was streaked on an LB solid culture medium (containing 10 µg/mL kanamycin) and was cultured in a 37° C. constant-temperature incubator for 18 h to obtain a single colony; the single colony was picked, an LB liquid culture medium (containing 10 µg/mL kanamycin) was inoculated with the single colony, culturing was performed in a 37° C. and 200 rpm shaker for 14 h, and activation continued for 3 generations to obtain an activated bacterial solution; an LB liquid culture medium (containing 10 µg/mL kanamycin) was inoculated with the activated bacterial solution according to the inoculation quantity of 1% (v/v), culturing was performed in the 37° C. and 200 rpm shaker for 14 h, so as to obtain a bacterial suspension; the obtained bacterial suspension was centrifuged under the conditions of 25° C. and 12000 g for 10 min to obtain wet bacterial cells; the pET-28a(+) vector in the wet bacterial cells was extracted by using a plasmid miniprep kit; and the obtained pET-28a(+) vector was re-dissolved through 50 µL of ddH$_2$O and was stored at −20° C.

The obtained pET-28a(+) vector and the bbi, bli, bpi and bdi genes obtained in example 2 were digested by using restriction enzymes Hind III and Nde I, and then digested and purified DNA was connected by utilizing T$_4$ ligase to obtain a connected product, wherein a specific connecting system is shown in Table 2.

The obtained connected product was connected overnight at 16° C. for 15 h, and then converted into a competent cell of *E. coli* DH5a; the converted competent cell of *E. coli* DH5a was coated with an LB solid culture medium (containing 10 µg/mL kanamycin) and inversely cultured at 37° C. for 24 h; and a positive transformant was picked, a plasmid was extracted, and a sequencing verification result showed successful connection, so that recombinant plasmids pET28a-bbi, pET28a-bli, pET28a-bpi and pET28a-bdi were obtained.

The obtained recombinant plasmids pET28a-bbi, pET28a-bli, pET28a-bpi and pET28a-bdi were guided into *E. coli* BL21 (DE3) respectively to obtain recombinant *E. coli* BL21 (DE3)/pET28a-bbi, *E. coli* BL21 (DE3)/pET28a-bli, *E. coli* BL21(DE3)/pET28a-bpi and *E. coli* BL21 (DE3)/pET28a-bdi.

The obtained recombinant *E. coli* BL21 (DE3)/pET28a-bbi, *E. coli* BL21 (DE3)/pET28a-b/i, *E. coli* BL21 (DE3)/pET28a-bpi and *E. coli* BL21 (DE3)/pET28a-bdi were streaked on an LB solid culture medium respectively and was cultured in a 37° C. constant-temperature incubator for 18 h, so as to obtain a single colony; the single colony was picked, an LB liquid culture medium was inoculated with the single colony, culturing was performed in a 37° C. and 200 rpm shaker for 14 h, and activation continued for 3 generations to obtain an activated bacterial solution; an LB liquid culture medium was inoculated with the activated bacterial solution according to the inoculation quantity of 1% (v/v), and culturing was performed under the conditions that the temperature was 37° C. and the rotating speed was 200 rpm for 12 h, so as to obtain fermentation broth; the fermentation broth was centrifuged under the conditions of 4° C. and 12000 g for 10 min to obtain wet bacterial cells; the wet bacterial cells were crushed and then centrifuged under the conditions of 4° C. and 12000 g for 10 min, to obtain a cell disruption supernatant; and the enzyme activity of linoleic acid isomerase in the obtained cell disruption supernatant was detected. Detection results are as follows:

The enzyme activity of the linoleic acid isomerase in the cell disruption supernatant obtained by fermenting the recombinant E. coli BL21 (DE3)/pET28a-bbi is 6.7 U/mg, the enzyme activity of the linoleic acid isomerase in the cell disruption supernatant obtained by fermenting the recombinant E. coli BL21 (DE3)/pET28a-bli is 1.7 U/mg, the enzyme activity of the linoleic acid isomerase in the cell disruption supernatant obtained by fermenting the recombinant E. coli BL21 (DE3)/pET28a-bpi is 1.8 U/mg, and the enzyme activity of the linoleic acid isomerase in the cell disruption supernatant obtained by fermenting the recombinant E. coli BL21 (DE3)/pET28a-bdi is 1.4 U/mg. It can be seen that the recombinant E. coli BL21 (DE3)/pET28a-bbi, E. coli BL21 (DE3)/pET28a-bli, E. coli BL21 (DE3)/pET28a-bpi and E. coli BL21 (DE3)/pET28a-bdi can all successfully express the linoleic acid isomerase.

TABLE 2

| Connecting System | | |
|---|---|---|
| Gene | Reagent | Dosage |
| bbi | 10 × reaction buffer | 2 μL |
|  | T4 ligase | 2 μL |
|  | Template volume | 11.26 μg |
|  | Plasmid volume | 5.26 μL |
| bli | 10 × reaction buffer | 2 μL |
|  | T4 ligase | 2 μL |
|  | Template volume | 12.81 μg |
|  | Plasmid volume | 3.19 μL |
| bpi | 10 × reaction buffer | 2 μL |
|  | T4 ligase | 2 μL |
|  | Template volume | 12.78 μg |
|  | Plasmid volume | 3.22 μL |
| bdi | 10 × reaction buffer | 2 μL |
|  | T4 ligase | 2 μL |
|  | Template volume | 13.22 μg |
|  | Plasmid volume | 2.78 μL |

Example 4. Application of Recombinant E. coli

An LB liquid culture medium was inoculated with activated bacterial solutions of the recombinant E. coli BL21 (DE3)/pET28a-bbi, E. coli BL21 (DE3)/pET28a-b/i, E. coli BL21 (DE3)/pET28a-bpi and E. coli BL21 (DE3)/pET28a-bdi obtained in example 3 respectively according to the inoculation quantity of 1% (v/v), culturing was performed under the conditions that the temperature was 37° C. and the rotating speed was 200 rpm until $OD_{600}$ was 0.4 to 0.6, and then IPTG with final concentrations of 0 mM, 0.05 mM, 0.1 mM, 0.3 mM, 0.5 mM, 0.8 mM and 1.0 mM was added into the culture medium respectively to continue inducing culture under the conditions of 18° C. and 200 rpm for 15 h, so as to obtain a culture solution; the culture solution was centrifuged under the conditions of 25° C. and 12000 g for 10 min to obtain wet bacterial cells; the wet bacterial cells were respectively re-suspended to a KPB solution (pH=6.5) according to a concentration of 0.5 mg wet bacterial cells/mL, and then linoleic acid with final concentrations of 0.01 mg/mL, 0.05 mg/mL, 0.1 mg/mL and 0.5 mg/mL were respectively added into the KPB solution to react for 3 h under the conditions of 37° C. and 200 rpm; and after reaction was finished, the conversion rate of conjugated linoleic acid in reaction solution was detected, and types and ratios of conjugated linoleic acid isomers in the obtained conjugated linoleic acid were detected. See FIGS. 1-5 for detection results.

It can be known from FIG. 1 that when the final concentration of the IPTG is 0.1 mM, the conversion rate of the conjugated linoleic acid in the reaction solution obtained by reaction on the recombinant E. coli BL21 (DE3)/pET28a-bbi, E. coli BL21 (DE3)/pET28a-bli, E. coli BL21 (DE3)/pET28a-bpi and E. coli BL21 (DE3)/pET28a-bdi is the highest.

It can be known from FIGS. 2-5 that when the final concentration of the IPTG is 0.1 mM, the conversion rate of the conjugated linoleic acid in the reaction solution obtained by reaction on the recombinant E. coli BL21 (DE3)/pET28a-bbi can reach 42.1%, wherein cis9, trans11-CLA accounts for 89.1%, trans10, cis12-CLA accounts for 1%, and trans9, trans11-CLA accounts for 9.9%.

When the final concentration of the IPTG is 0.1 mM, the conversion rate of the conjugated linoleic acid in the reaction solution obtained by reaction on the recombinant E. coli BL21 (DE3)/pET28a-bli is 12.1%, wherein cis9, trans11-CLA accounts for 84.3%, trans10, cis12-CLA accounts for 1.2%, and trans9, trans11-CLA accounts for 4.5%.

When the final concentration of the IPTG is 0.1 mM, the conversion rate of the conjugated linoleic acid in the reaction solution obtained by reaction on the recombinant E. coli BL21 (DE3)/pET28a-bpi is 19.5%, wherein cis9, trans11-CLA accounts for 88.9%, trans10, cis12-CLA accounts for 0.98%, and trans9, trans11-CLA accounts for 10.1%.

When the final concentration of the IPTG is 0.1 mM, the conversion rate of the conjugated linoleic acid in the reaction solution obtained by reaction on the recombinant E. coli BL21 (DE3)/pET28a-bdi is 13.5%, wherein cis9, trans11-CLA accounts for 87.1%, trans10, cis12-CLA accounts for 1.3%, and trans9, trans11-CLA accounts for 11.6%.

Example 5. Expression of Linoleic Acid Isomerase in *Yarrowia lipolytica* Strain According to codon preference of *Yarrowia lipolytica*, a bbi gene is optimized by utilizing Genscript OptimumGene™ software, a codon adaptation index is increased from 0.80 to 0.96 after optimization, and the optimized gene is named an obbi gene.

Figure 6:
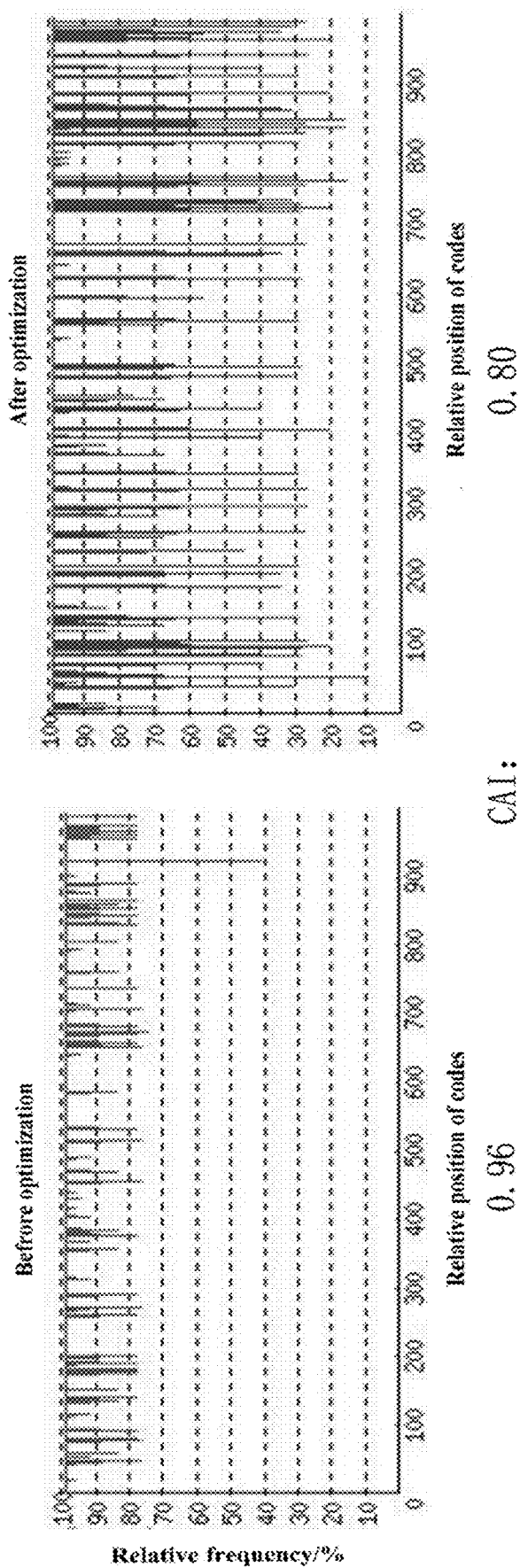
FIG. 6: CAI maps of bbi sequences before and after codon optimization.

The obbi gene is complete-gene synthesized by Nanjing GenScript Biotech Co., Ltd., and cloned to a vector pUC57 to obtain a recombinant plasmid pUC57-obbi. A nucleotide sequence of the bbi gene is shown in SEQ ID NO: 5, a nucleotide sequence of the obbi gene is shown in SEQ ID NO: 17, and CAI maps of the bbi gene and the obbi gene are shown in FIG. 6.

Figure 7:
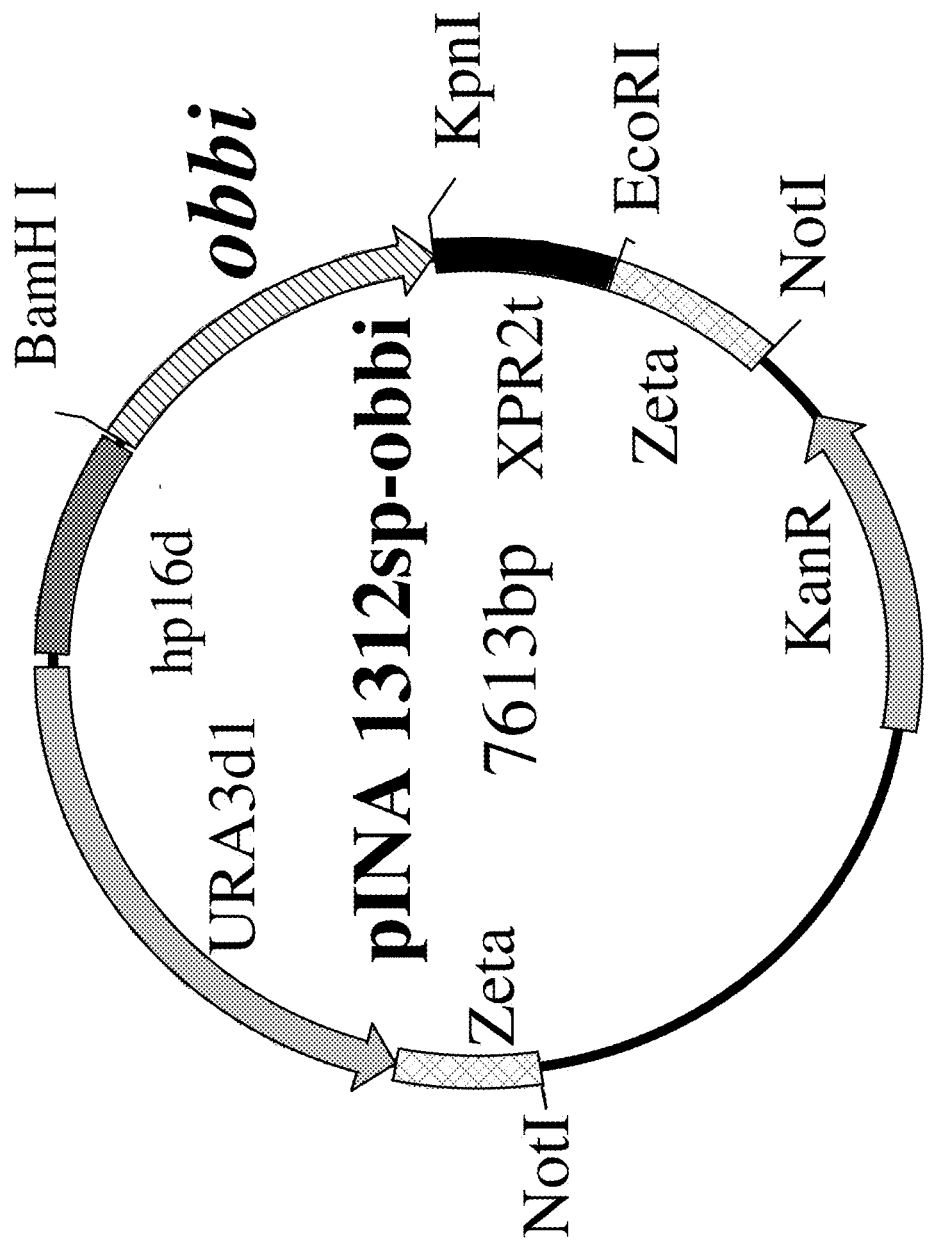
FIG. 7: A plasmid map of a recombinant plasmid pINA 1312sp-obbi.
Figure 8:
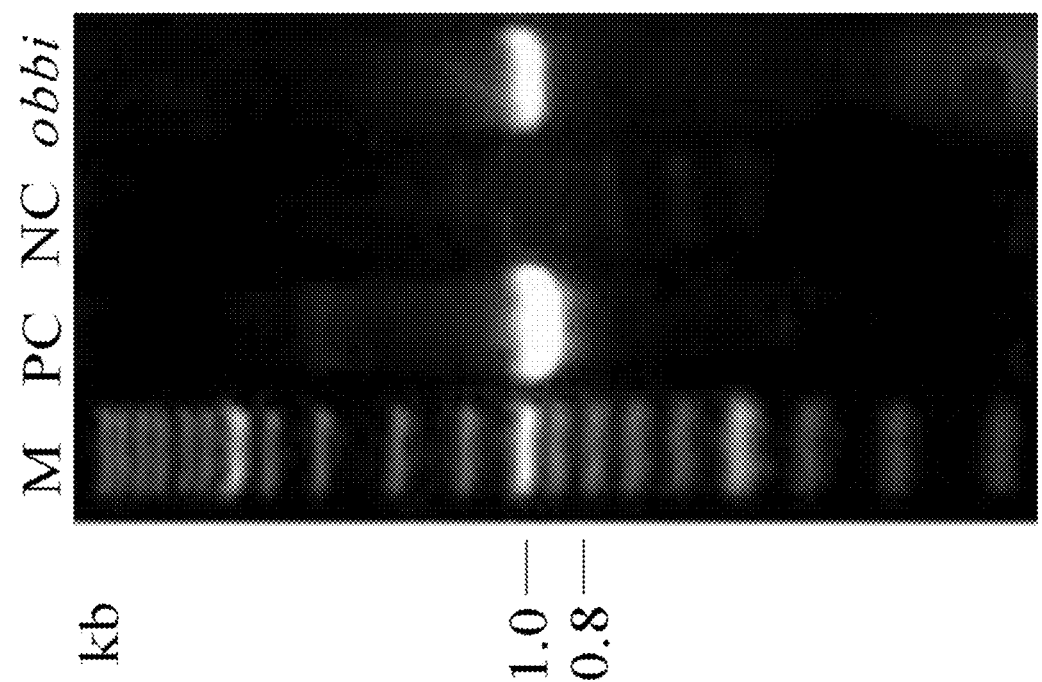
FIG. 8: A PCR verification result of the recombinant plasmid pINA 1312sp-obbi.

The pINA 1312sp plasmid and the recombinant plasmid pUC57-obbi were digested by using restriction enzymes BamH I and Kpn I, and then digested and purified DNA was connected by utilizing $T_4$ ligase to obtain a connected product; the obtained connected product was connected overnight at 16° C. for 15 h and then converted to a competent cell of E. coli DH5a; an LB solid culture medium (containing 10 μg/mL kanamycin) was coated with the converted competent cell of the E. coli DH5a to be inversely cultured at 37° C. for 12 to 16 h; and a positive transformant was picked, a plasmid was extracted, and a sequencing verification result showed successful connection, so that recombinant plasmid pINA 1312sp-obbi was obtained. See FIG. 7 for a plasmid map of the recombinant plasmid pINA 1312sp-obbi, and see FIG. 8 for verification results.

Figure 9:
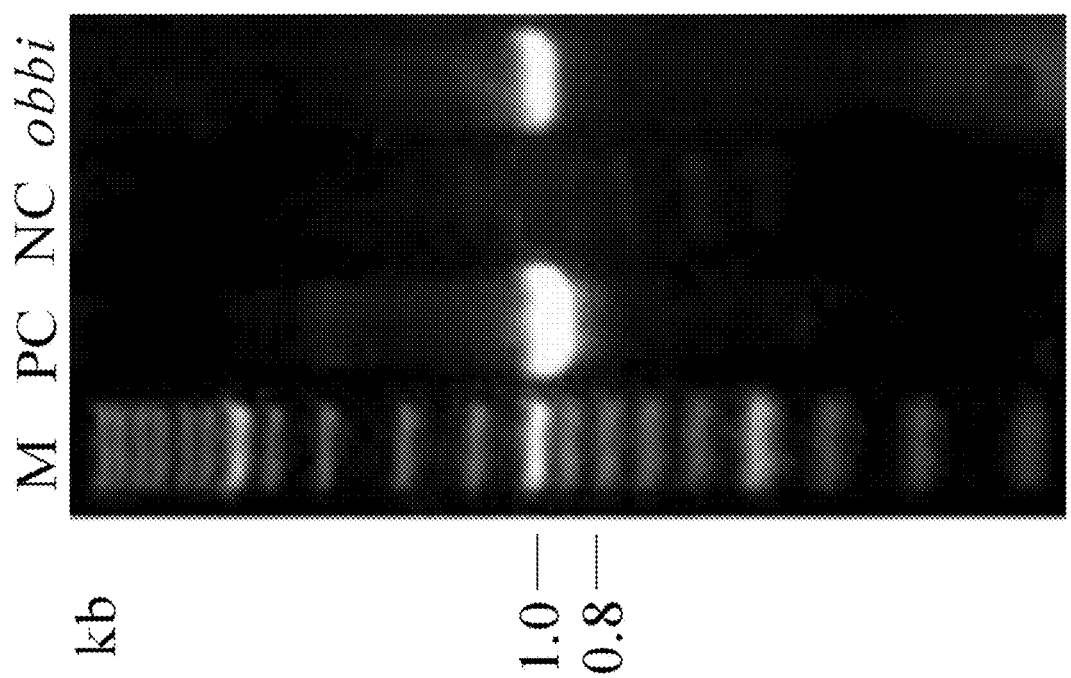
FIG. 9: A PCR verification result of a recombinant Yarrowia lipolytica strain Yarrowia lipolytica/pINA 1312sp-obbi.

The obtained recombinant plasmid pINA 1312sp-obbi was guided into *Yarrowia lipolytica*; the converted *Yarrowia lipolytica* was streaked on a YNBD solid culture medium and was cultured in a 28° C. constant-temperature incubator for 2 to 3 d; and a positive transformant was picked, a YNBD liquid culture medium was inoculated with the positive transformant, culturing was performed at 28° C. and 200 rpm for 2 d, bacterial cells were collected, a genome was extracted, the genome of the transformant was subjected to PCR verification by using verification primers P1/P2 (a nucleotide sequence of P1 is shown in SEQ ID NO: 6: ATACAAGAGCGTTTGCCAGC, and a nucleotide sequence of P2 is shown in SEQ ID NO: 7: CCTTGGTCCAGGGGTTGA), and verification was correct, so that a recombinant *Yarrowia lipolytica* strain *Yarrowia lipolytica*/pINA 1312sp-obbi was obtained (20 transformants verified to be correct were totally obtained). See FIG. 9 for verification results.

The recombinant *Yarrowia lipolytica* strain *Yarrowia lipolytica*/pINA 1312sp-obbi was streaked on a YNBD solid culture medium and was cultured in a 28° C. constant-temperature incubator for 2 to 3 d; a positive transformant was picked, a YNBD liquid culture medium was inoculated with the positive transformant, and culturing was performed at 28° C. and 200 rpm for 2 d; a 5 mL YPD culture medium was inoculated with a seed solution according to the inoculation quantity of 1% (v/v), and culturing was performed at 28° C. and 200 rpm for 36 h so as to obtain fermentation broth; the fermentation broth was centrifuged under the conditions of 25° C. and 12000 g for 10 min to obtain wet bacterial cells; the wet bacterial cells were crushed and then centrifuged under the conditions of 25° C. and 12000 g for 10 min to obtain a cell disruption supernatant; and the specific enzyme activity of linoleic acid isomerase in the obtained cell disruption supernatant was detected. Detection results are as follows:

The specific enzyme activity of the linoleic acid isomerase in the cell disruption supernatant obtained by fermenting the recombinant *Yarrowia lipolytica* strain *Yarrowia lipolytica*/pINA 1312sp-obbi is 2.31 U/mg. It can be seen that the recombinant *Yarrowia lipolytica* strain *Yarrowia lipolytica*/pINA 1312sp-obbi can successfully express the linoleic acid isomerase.

Example 6. Application of Recombinant *Yarrowia lipolytica* Strain

1. Linoleic Acid as Substrate

Using a recombinant *Yarrowia lipolytica* strain *Yarrowia lipolytica*/pINA 1312sp containing an empty plasmid as control, a recombinant *Yarrowia lipolytica* strain *Yarrowia lipolytica*/pINA 1312sp-obbi was streaked on a YNBD solid culture medium and was cultured in a 28° C. constant-temperature incubator for 2 to 3 d; a single colony was picked, a YNBD liquid culture medium was inoculated with the single colony, and culturing was performed at 28° C. and 200 rpm for 2 d; a 5 mL YPD culture medium was inoculated with a seed solution according to the inoculation quantity of 1% (v/v), culturing was performed at 28° C. and 200 rpm for 36 h, and then free linoleic acid with a final concentration of 0.5 g/L was added into the culture medium to continue culture at 28° C. and 200 rpm for 36 h so as to obtain fermentation broth; the fermentation broth was centrifuged under the conditions of 25° C. and 12000 g for 10 min to obtain wet bacterial cells; and the wet bacterial cells were washed twice with 0.85% NaCl, and then yields of cis9, trans11-CLA, trans10, cis12-CLA, and trans9, trans11-CLA in a cell, as well as ratios of the contents of the cis9, trans11-CLA, trans10, cis12-CLA, and trans9, trans11-CLA accounting for the content of total conjugated fatty acid produced were detected. See FIGS. 10-11 and 14 for detection results.

Figure 10:
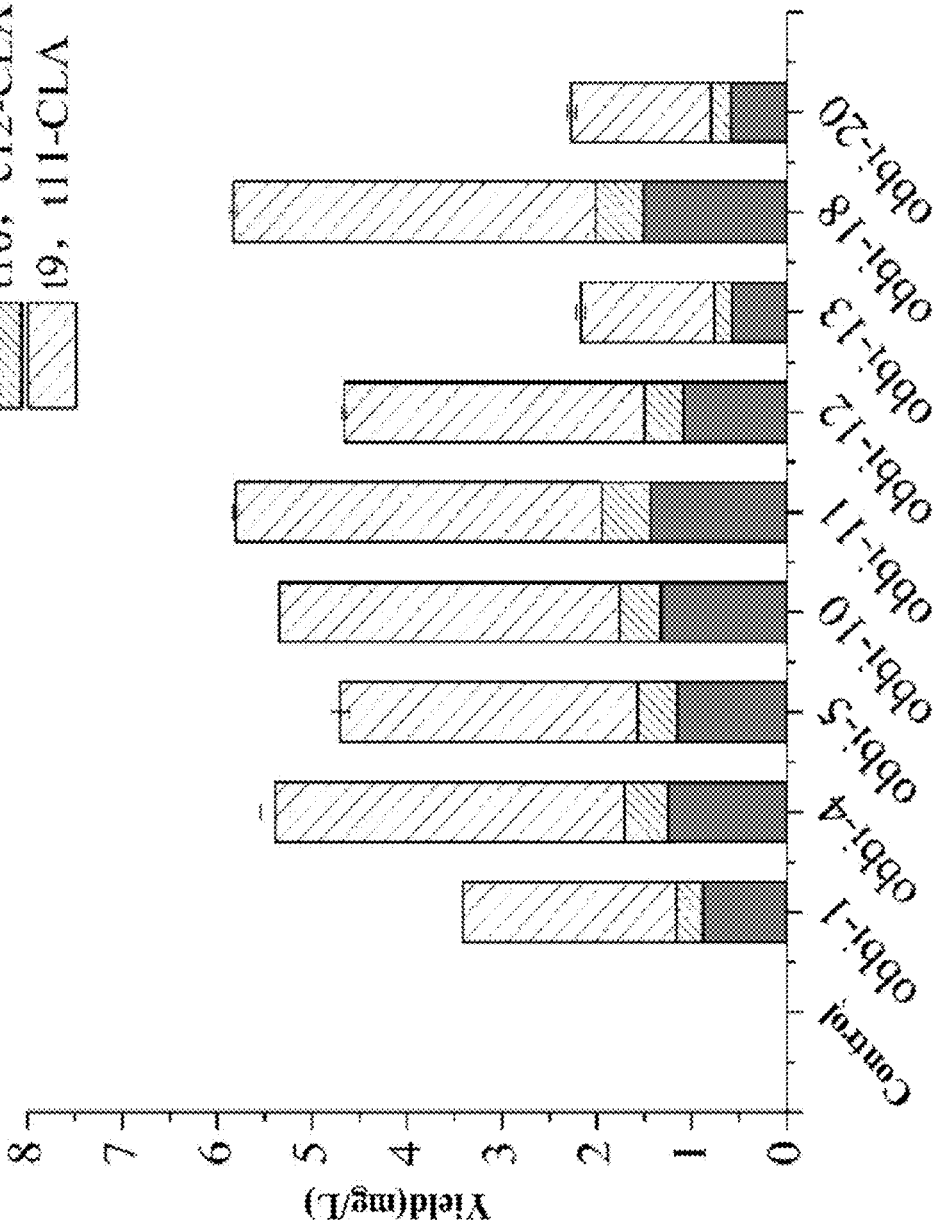
FIG. 10: Yields of cis9, trans11-CLA, trans10, cis12-CLA and trans9, trans11-CLA produced by a recombinant Yarrowia lipolytica strain Yarrowia lipolytica/pINA 1312sp-obbi with free fatty acid as a substrate.
Figure 11:
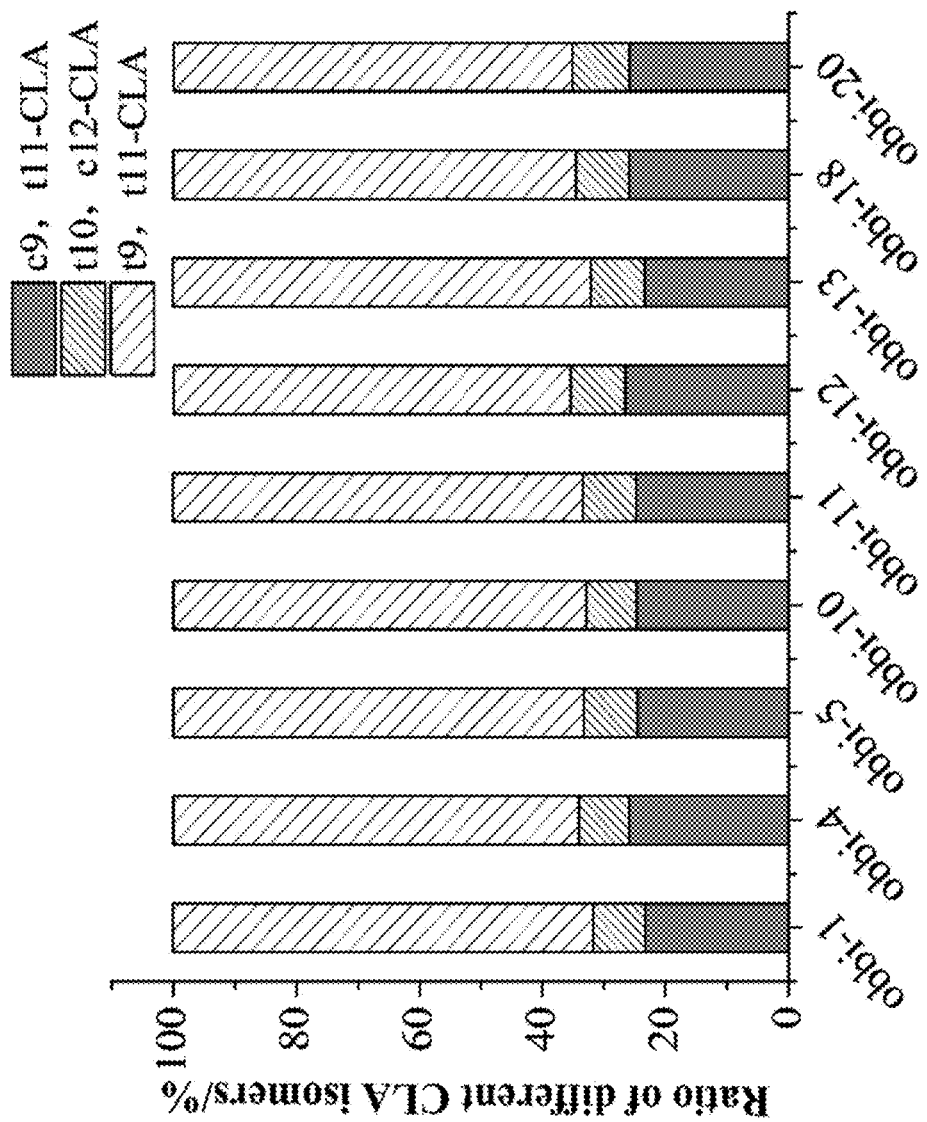
FIG. 11: Ratios of cis9, trans11-CLA, trans10, cis12-CLA and trans9, trans11-CLA in total conjugated fatty acid produced by a recombinant Yarrowia lipolytica strain Yarrowia lipolytica/pINA 1312sp-obbi with free fatty acid as a substrate.
Figure 14:
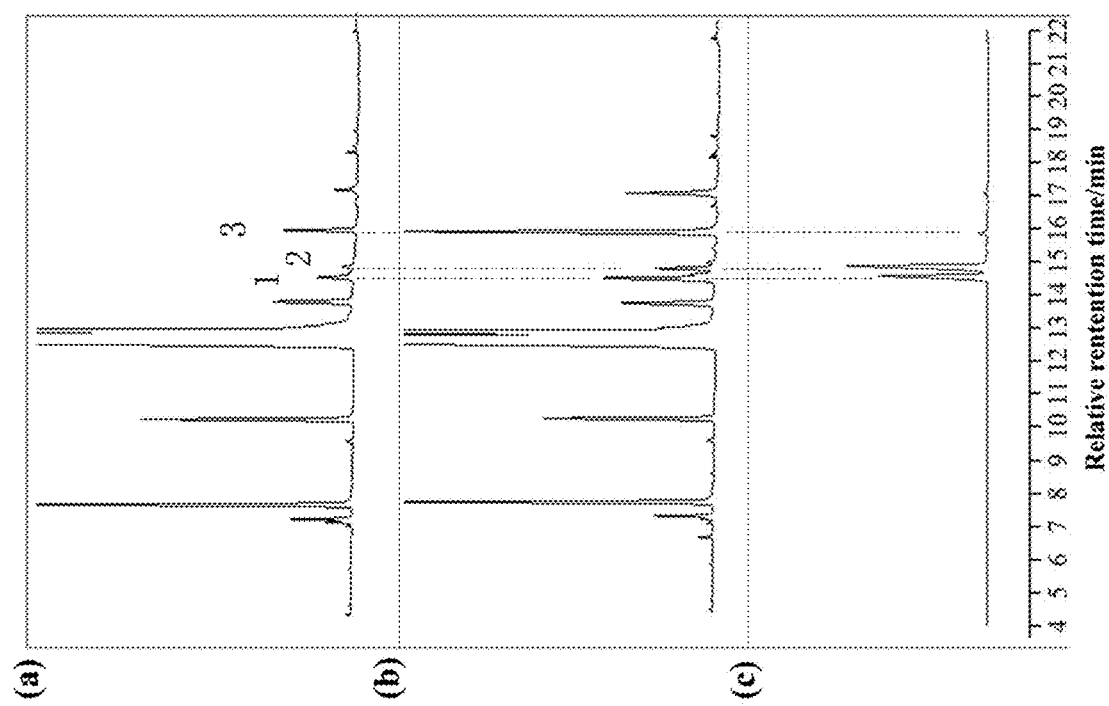
FIG. 14: GC-MS identification maps of conjugated linoleic acid produced by a recombinant Yarrowia lipolytica strain Yarrowia lipolytica/pINA 1312sp-obbi using different substrates, wherein (a) represents a GC-MS identification map of conjugated linoleic acid produced by Yarrowia lipolytica/pINA 1312sp-obbi with free fatty acid as a substrate, (b) represents a GC-MS identification map of conjugated linoleic acid produced by the recombinant Yarrowia lipolytica strain Yarrowia lipolytica/pINA 1312sp-obbi with safflower oil as a substrate, and (c) represents a composition chromatogram of fatty acid in a sample (the sample is a conjugated linoleic acid standard substance purchased from Sigma), and numbers 1, 2 and 3 respectively represent cis9, trans11-CLA, trans10, cis12-CLA, and trans9, trans11-CLA.

It can be known from FIGS. 10-11 and 14 that the yields of the cis9, trans11-CLA, trans10, cis12-CLA, and trans9, trans11-CLA produced by the recombinant *Yarrowia lipolytica* strain *Yarrowia lipolytica*/pINA 1312sp-obbi with the free fatty acid as the substrate are respectively 1.5 mg/L, 0.5 mg/L and 3.8 mg/L, wherein the content of the cis9, trans11-CLA accounts for 25% of the total amount of conjugated fatty acid, the content of the trans10, cis12-CLA accounts for 9% the total amount of conjugated fatty acid, and the content of the trans9, trans11-CLA accounts for 66% of the total amount of conjugated fatty acid.

2. Safflower Oil as Substrate

Using a recombinant *Yarrowia lipolytica* strain *Yarrowia lipolytica*/pINA 1312sp containing an empty plasmid as control, a recombinant *Yarrowia lipolytica* strain *Yarrowia* lipolytica/pINA 1312sp-obbi was streaked on a YNBD solid culture medium and was cultured in a 28° C. constant-temperature incubator for 2 to 3 d; a single colony was picked, a YNBD liquid culture medium was inoculated with the single colony, and culturing was performed at 28° C. and 200 rpm for 2 d; a 5 mL YPD culture medium was inoculated with a seed solution according to the inoculation quantity of 1% (v/v), culturing was performed at 28° C. and 200 rpm for 36 h, and then safflower oil with a final concentration of 20 g/L was added into the culture medium to continue culture at 28° C. and 200 rpm for 36 h so as to obtain fermentation broth; the fermentation broth was centrifuged under the conditions of 25° C. and 12000 g for 10 min to obtain wet bacterial cells; and the wet bacterial cells were washed twice with 0.85% NaCl, and then yields of cis9, trans11-CLA, trans10, cis12-CLA, and trans9, trans11-CLA in a cell, as well as ratios of the contents of the cis9, trans11-CLA, trans10, cis12-CLA, and trans9, trans11-CLA accounting for the content of total conjugated fatty acid produced were detected. See FIGS. 12-14 for detection results.

Figure 12:
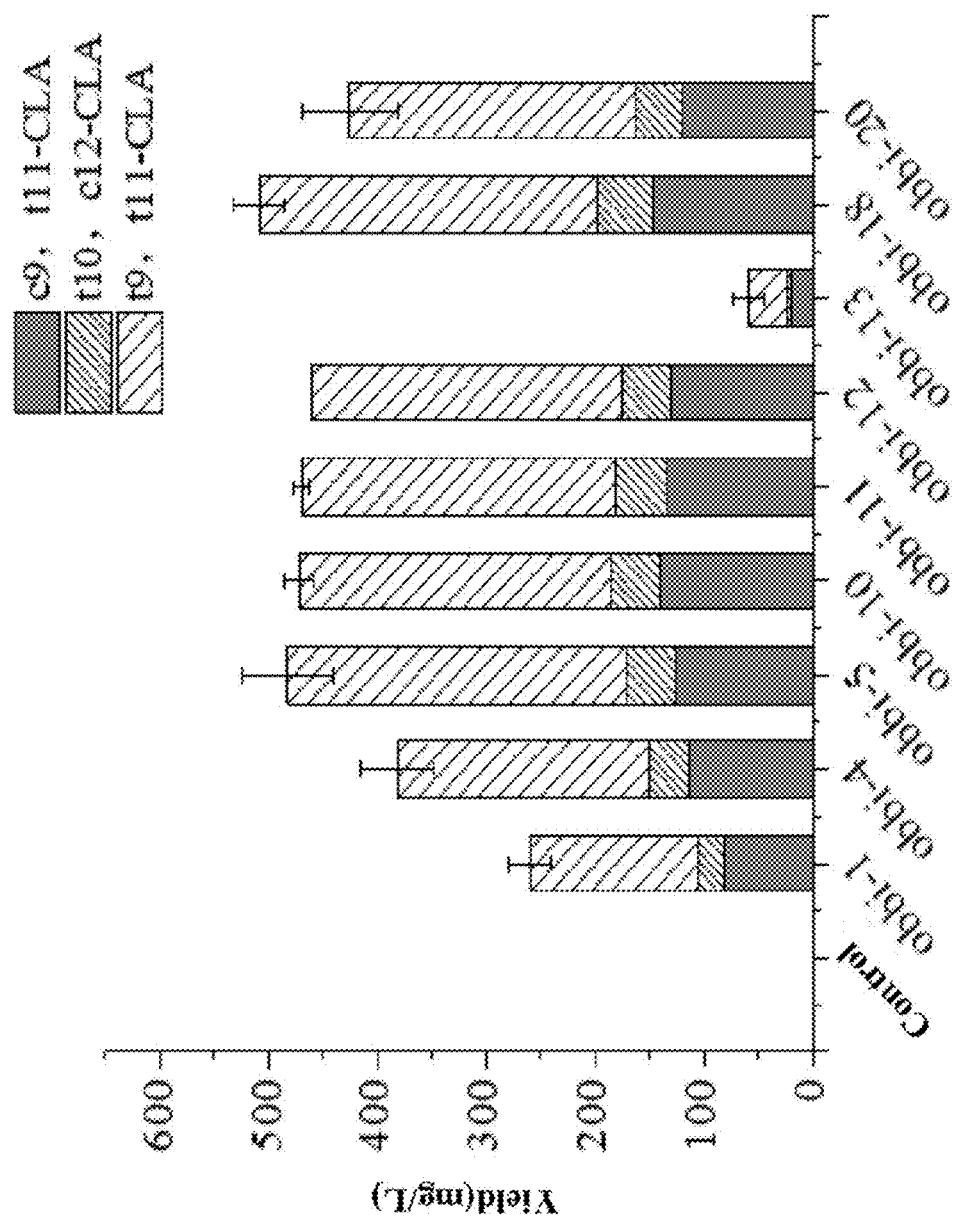
FIG. 12: Yields of cis9, trans11-CLA, trans10, cis12-CLA and trans9, trans11-CLA produced by a recombinant Yarrowia lipolytica strain Yarrowia lipolytica/pINA 1312sp-obbi with safflower oil as a substrate.
Figure 13:
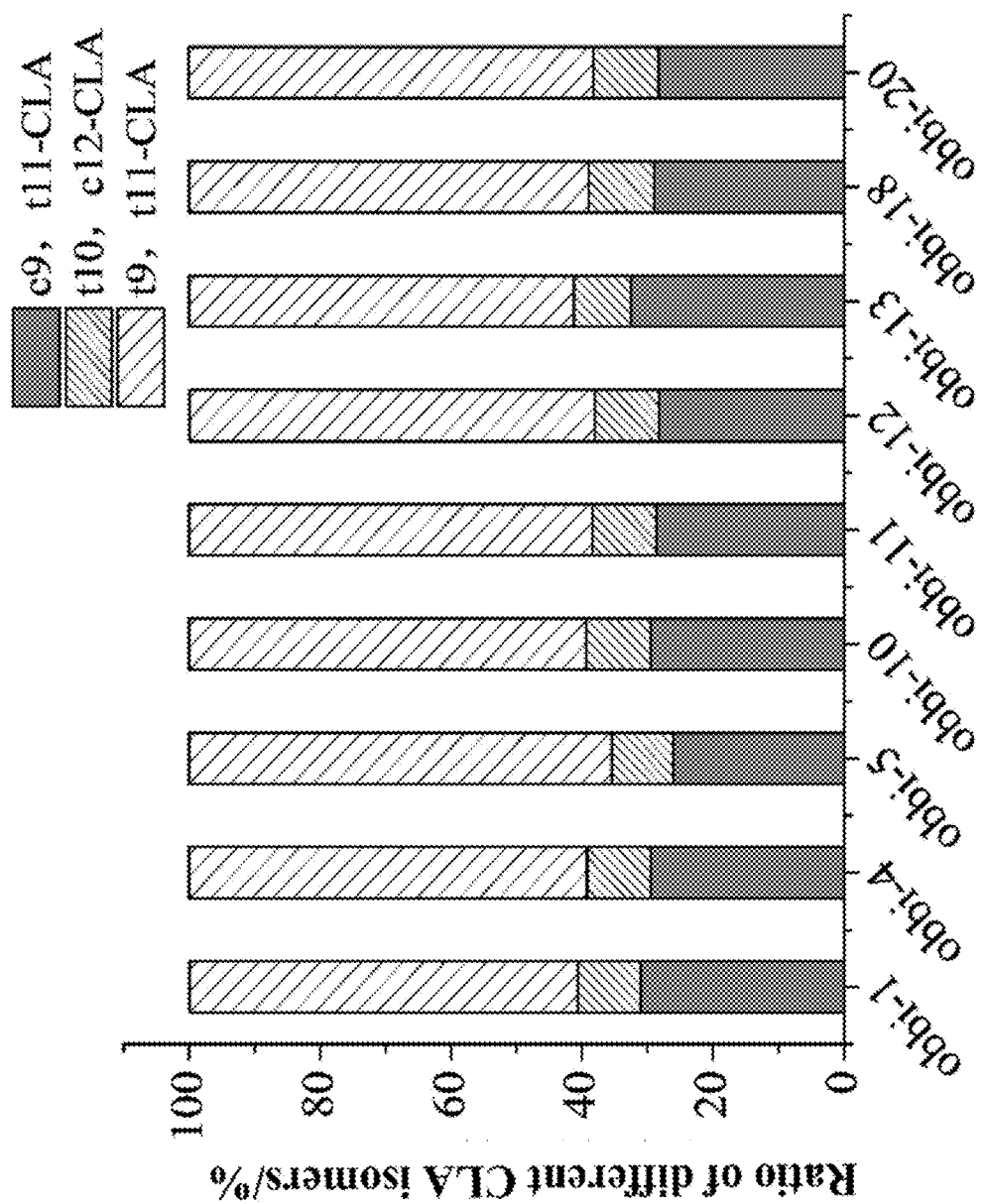
FIG. 13: Percentages of cis9, trans11-CLA, trans10, cis12-CLA and trans9, trans11-CLA in total conjugated fatty acid produced by a recombinant Yarrowia lipolytica strain Yarrowia lipolytica/pINA 1312sp-obbi with safflower oil as a substrate.

It can be known from FIGS. 12-14 that the yields of the cis9, trans11-CLA, trans10, cis12-CLA, and trans9, trans11-CLA produced by the recombinant *Yarrowia lipolytica* strain *Yarrowia* lipolytica/pINA 1312sp-obbi with the safflower oil as the substrate are respectively 146.8 mg/L, 50.9 mg/L and 310.7 mg/L, wherein the content of the cis9, trans11-CLA accounts for 30% of the content of the total conjugated fatty acid, the content of the trans10, cis12-CLA accounts for 10% of the content of the total conjugated fatty acid, and the content of the trans9, trans11-CLA accounts for 60% of the content of the total conjugated fatty acid.

3. Enlarged Cultivation

A recombinant *Yarrowia lipolytica* strain *Yarrowia lipolytica*/pINA 1312sp-obbi was streaked on a YNBD solid culture medium and were cultured in a 28° C. constant-temperature incubator for 2 to 3 d; a single colony was picked, a YNBD liquid culture medium was inoculated with the single colony, and culturing was performed at 28° C. and 200 rpm for 2 d; a 50 mL YPD culture medium was inoculated with a seed solution according to the inoculation quantity of 1% (v/v), culturing was performed at 28° C. and 200 rpm for 36 h, and then safflower oil with a final concentration of 20 g/L was added into the culture medium to continue culture at 28° C. and 200 rpm for 36 h so as to obtain fermentation broth; the fermentation broth was centrifuged under the conditions of 25° C. and 12000 g for 10 min to obtain wet bacterial cells; and the wet bacterial cells were washed twice with 0.85% NaCl, and then yields of cis9, trans11-CLA, trans10, cis12-CLA, and trans9, trans11-

CLA in a cell, as well as ratios of cis9, trans11-CLA, trans10, cis12-CLA, and trans9, trans11-CLA in total conjugated fatty acid produced were detected. Detection results are as follows:

The yields of the cis9, trans11-CLA, trans10, cis12-CLA, and trans9, trans11-CLA produced by the recombinant *Yarrowia lipolytica* strain *Yarrowia lipolytica*/pINA 1312sp-obbi with the safflower oil as the substrate are respectively 224.0 mg/L, 73.7 mg/L and 454.0 mg/L, wherein cis9, trans11-CLA accounts for 29.8% of the total conjugated fatty acid, trans10, cis12-CLA accounts for 9.8% of total conjugated fatty acid, and trans9, trans11-CLA accounts for 60.4% of total conjugated fatty acid.

Figure 15:
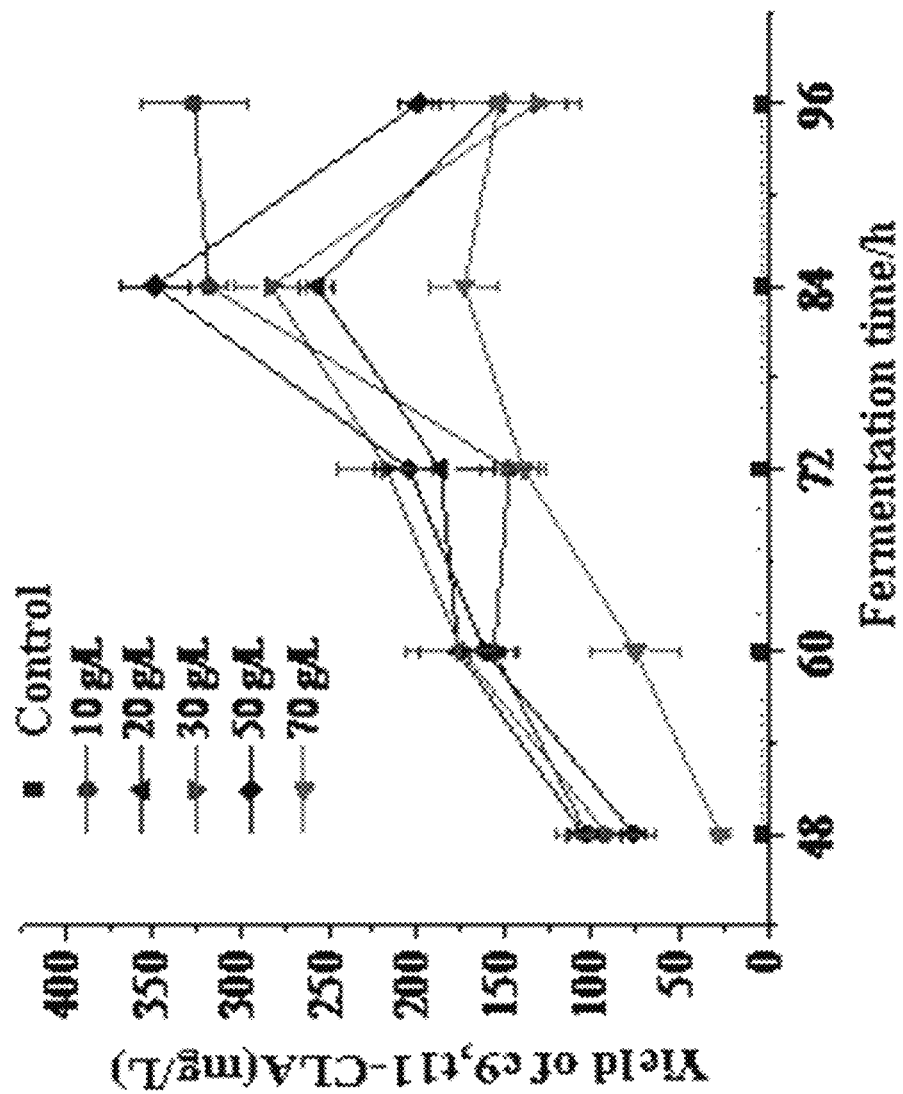
FIG. 15: Effects of concentration of safflower oil on the yield of cis9, trans11-CLA produced by a recombinant Yarrowia lipolytica strain Yarrowia lipolytica/pINA 1312sp-obbi.
Figure 16:
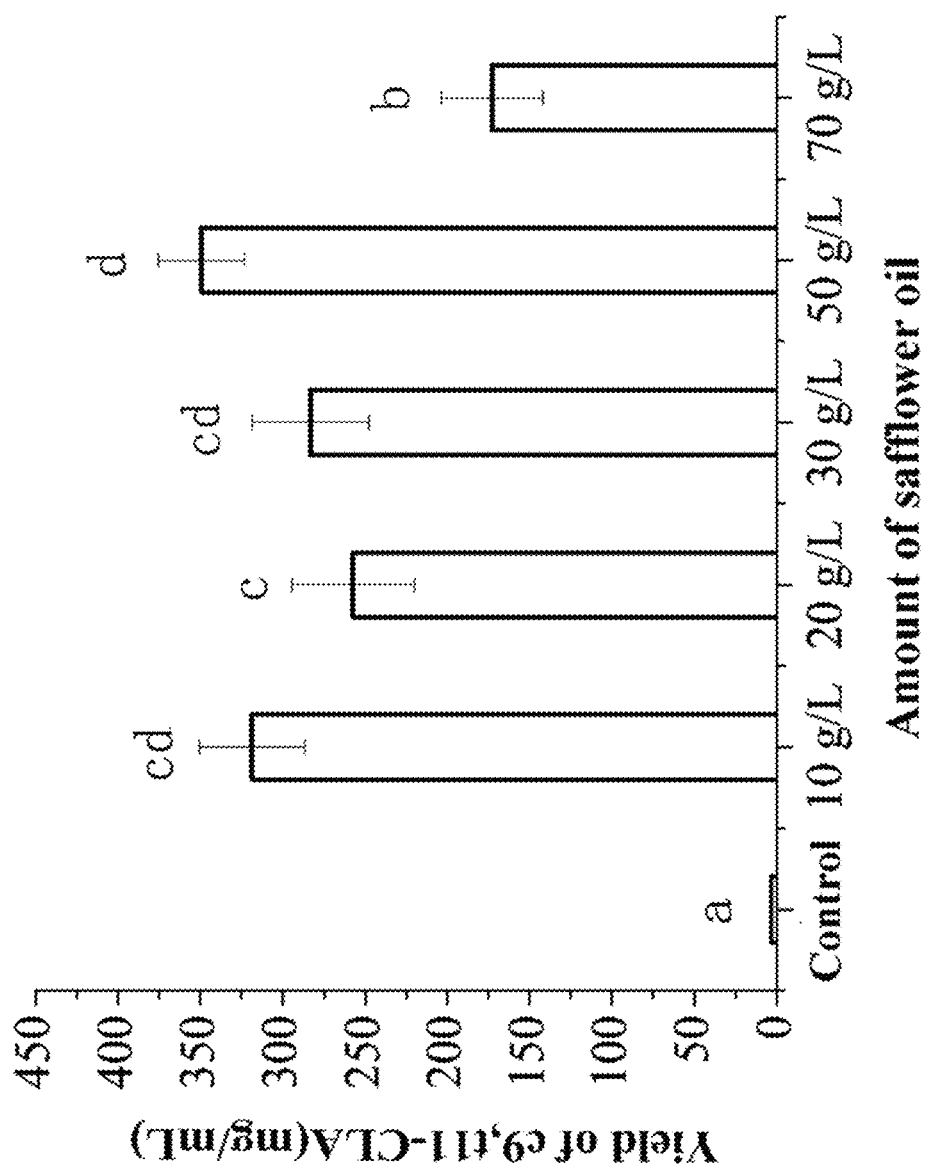
FIG. 16: Effects of concentration of safflower oil on the yield of cis9, trans11-CLA produced by a recombinant Yarrowia lipolytica strain Yarrowia lipolytica/pINA 1312sp-obbi at the 84th hour of fermentation.
Figure 17:
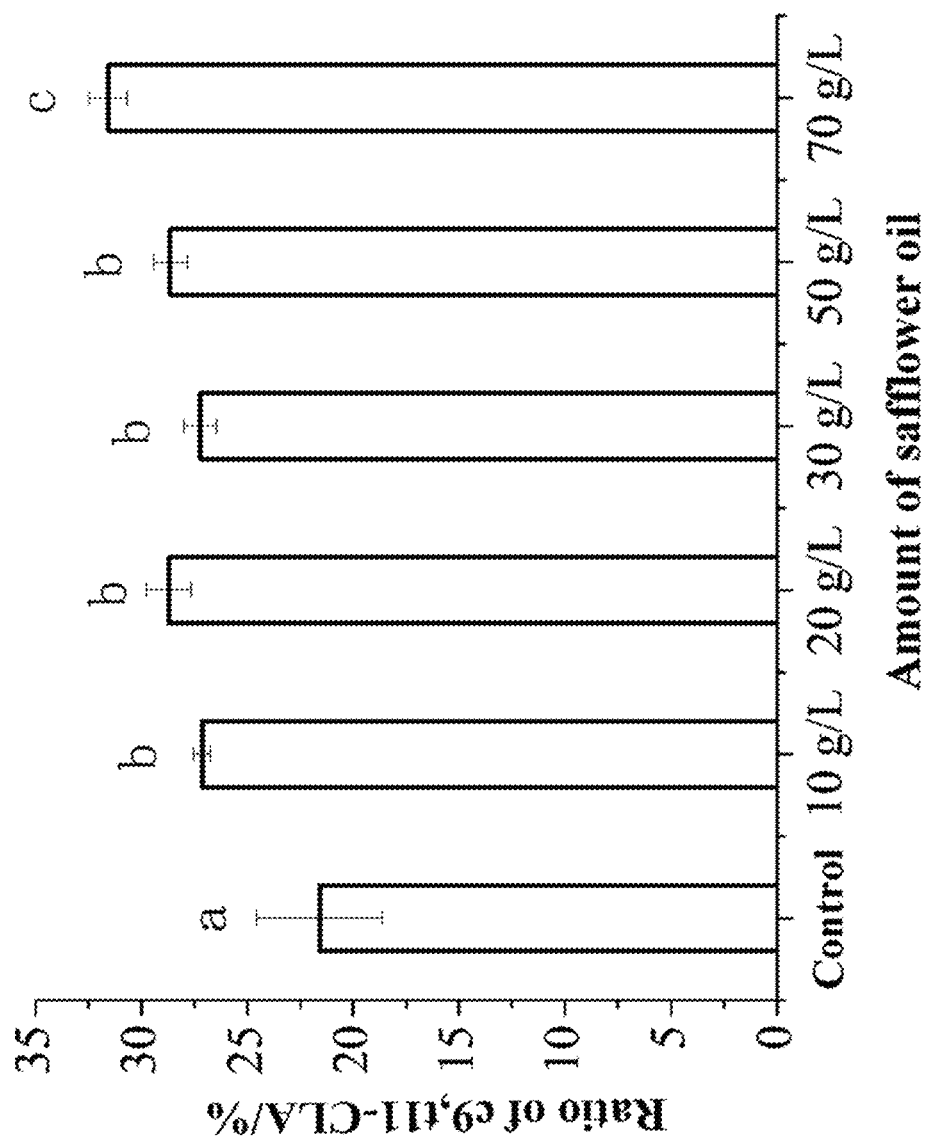
FIG. 17: Effects of concentration of safflower oil on the percentage of the yield of cis9, trans11-CLA in total conjugated fatty acid produced by a recombinant Yarrowia lipolytica strain Yarrowia lipolytica/pINA 1312sp-obbi at the 84th hour of fermentation.
Figure 18:
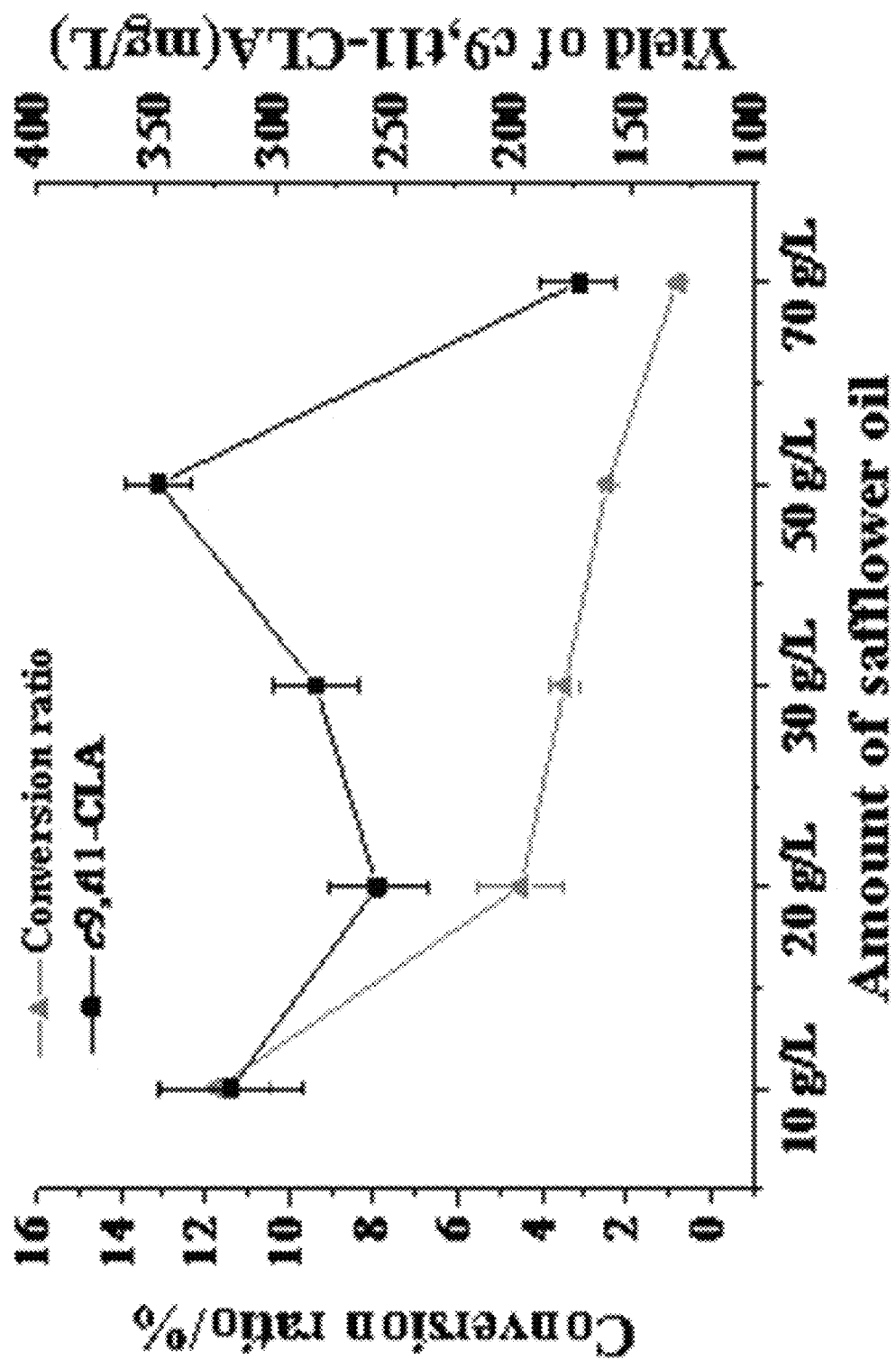
FIG. 18: Effects of concentration of safflower oil on the yield and the conversion rate of cis9, trans11-CLA produced by a recombinant Yarrowia lipolytica strain Yarrowia lipolytica/pINA 1312sp-obbi.

4. Influence of Concentration of Safflower Oil on Yield and Conversion Rate of Cis9, Trans11-CLA Produced by Recombinant *Yarrowia lipolytica* Strain *Yarrowia lipolytica*/pINA 1312sp-obbi The recombinant *Yarrowia lipolytica* strain *Yarrowia lipolytica*/pINA 1312sp-obbi was streaked on a YNBD solid culture medium and was cultured in a 28° C. constant-temperature incubator for 2 to 3 d; a single colony was picked, a YNBD liquid culture medium was inoculated with the single colony, and culturing was performed at 28° C. and 200 rpm for 2 d; a 50 mL YPD culture medium was inoculated with a seed solution according to the inoculation quantity of 1% (v/v), culturing was performed at 28° C. and 200 rpm for 36 h, then safflower oil with final concentrations of 10 g/L, 20 g/L, 30 g/L, 50 g/L and 70 g/L was respectively added into the culture medium to continue culture at 28° C. and 200 rpm, and 50 mL of fermentation broth was taken every 12 h; the fermentation broth was centrifuged under the conditions of 25° C. and 12000 g for 10 min to obtain wet bacterial cells; and the wet bacterial cells were washed twice with 0.85% NaCl, and then yields of cis9, trans11-CLA, trans10, cis12-CLA, and trans9, trans11-CLA in a cell, as well as ratios of the contents of the cis9, trans11-CLA, trans10, cis12-CLA, and trans9, trans11-CLA accounting for the content of total conjugated fatty acid produced were detected. See FIG. 15 for results of the influence of the concentration of the safflower oil on the yield of the cis9, trans11-CLA produced by the recombinant *Yarrowia lipolytica* strain *Yarrowia lipolytica*/pINA 1312sp-obbi. See FIG. 16 for the influence of the concentration of the safflower oil on the yield of the cis9, trans11-CLA produced by the recombinant *Yarrowia lipolytica* strain *Yarrowia lipolytica*/pINA 1312sp-obbi at the 84th h of fermentation. See FIG. 17 for the influence of the concentration of the safflower oil on a ratio of the yield of the cis9, trans11-CLA produced by the recombinant *Yarrowia lipolytica* strain *Yarrowia lipolytica*/pINA 1312sp-obbi at the 84th h of fermentation accounting for the yield of the total conjugated fatty acid produced. See FIG. 18 for the influence of the concentration of the safflower oil on the yield and the conversion rate of the cis9, trans11-CLA produced by the recombinant *Yarrowia lipolytica* strain *Yarrowia lipolytica*/pINA 1312sp-obbi.

It can be known from FIGS. 15-18 that when fermentation time is 84 h and the adding concentration of the safflower oil is 50 g/L, the content of the cis9, trans11-CLA is the highest, reaching 350 mg/L; and at the moment, the ratio of the content of the cis9, trans11-CLA accounting for the total CLA reaches 27.5%.

Example 7. Expression of Linoleic Acid Isomerase in *Lactobacillus plantarum*

On the premise of not affecting expression protein, the content of GC in the bbi obtained in example 2 was reduced, a corresponding codon was made to be more suitable for biological utilization of *lactobacillus*, codon optimization and gene sequence synthesis were completed by General Biol System (Anhui) Co., Ltd., digestion sites at two ends of the sequence were Kpn I and Xba I respectively, the sequence was connected into the pU57 plasmid, and the plasmid was stored in *E. coli* DH5α to obtain recombinant *E. coli* DH5α/pU57-bbi (U). A nucleotide sequence of a non-optimized bbi sequence is shown in SEQ ID NO: 5, and a nucleotide sequence of an optimized bbi sequence is shown in SEQ ID NO: 18.

The pNZ44 plasmid was guided into *E. coli* DH5α to obtain *E. coli* DH5α/pNZ44; the *E. coli* DH5α/pNZ44 was streaked on an LB solid culture medium (containing 10 μg/mL kanamycin) and was cultured in a 37° C. constant-temperature incubator for 18 h to obtain a single colony; the single colony was picked, an LB liquid culture medium (containing 10 μg/mL kanamycin) was inoculated with the single colony, culturing was performed in a 37° C. and 200 rpm shaker for 14 h, and activation continued for 3 generations to obtain an activated bacterial solution; an LB liquid culture medium (containing 10 μg/mL kanamycin) was inoculated with the activated bacterial solution according to the inoculation quantity of 1% (v/v), and culturing was performed in the 37° C. and 200 rpm shaker for 14 h, so as to obtain a bacterial suspension; the obtained bacterial suspension was centrifuged under the conditions of 25° C. and 12000 g for 10 min to obtain wet bacterial cells; the pNZ44 plasmid in the wet bacterial cells was extracted by using a plasmid miniprep kit; and the obtained pNZ44 plasmid was re-dissolved through 50 μL of ddH$_2$O and was stored at −20° C.

The recombinant plasmid pU57-bbi (U) in the recombinant *E. coli* DH5α/pU57-bbi (U) was extracted by using the plasmid miniprep kit; and the obtained recombinant plasmid pU57-bbi (U) was re-dissolved by using 50 μL of ddH$_2$O and was stored at −20° C.

The obtained pNZ44 plasmid and the recombinant plasmid pU57-bbi (U) were digested by using restriction enzymes Kpn I and Xba I, and then digested and purified DNA was connected by utilizing T$_4$ ligase to obtain a connected product, wherein a specific connecting system is shown in Table 3.

Figure 19:
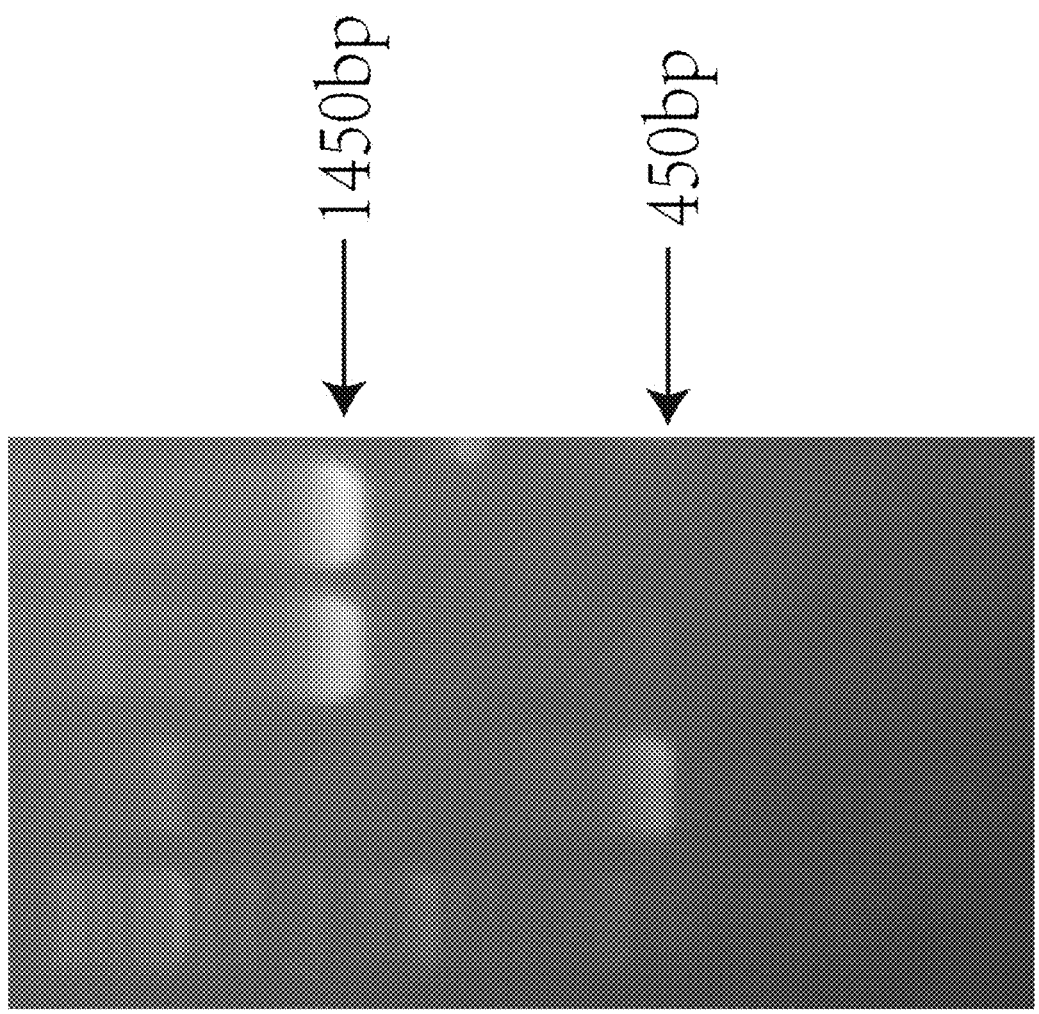
FIG. 19: A PCR verification result of recombinant plasmids pNZ44-bbi and pNZ44-bbi (U).

The obtained connected product was connected overnight at 16° C. for 15 h, and then converted into a competent cell of the *E. coli* DH5α; an LB solid culture medium (containing 10 μg/mL chloramphenicol) was coated with the converted competent cell of the *E. coli* DH5α and inversely cultured at 37° C. for 24 h; and a positive transformant was picked, a plasmid was extracted, and a sequencing verification result showed successful connection, so that the recombinant plasmid pNZ44-bbi, and the recombinant plasmid pNZ44-bbi (U) were obtained. See FIG. 19 for verification results.

The obtained recombinant plasmid pNZ44-bbi and recombinant plasmid pNZ44-bbi (U) were respectively guided into *Lactobacillus plantarum* ST-III, to obtain a *Lactobacillus plantarum* engineered strain *Lactobacillus plantarum* ST-III/pNZ44-bbi and a *Lactobacillus plantarum* engineered strain *Lactobacillus plantarum* ST-III/pNZ44-bbi (U).

The obtained *Lactobacillus plantarum* engineered strain *Lactobacillus plantarum* ST-III/pNZ44-bbi and *Lactobacillus plantarum* engineered strain *Lactobacillus plantarum* ST-III/pNZ44-bbi (U) were streaked on an MRS solid culture medium respectively and was cultured in a 37° C. constant-temperature incubator for 18 h, so as to obtain a single colony; the single colony was picked, an MRS liquid culture medium was inoculated with the single colony, culturing was performed in a 37° C. and 200 rpm shaker for 14 h, and activation continued for 3 generations to obtain an activated bacterial solution; an LB liquid culture medium was inoculated with the activated bacterial solution according to the inoculation quantity of 1% (v/v) to be stationarily cultured at 37° C. for 12 h, so as to obtain fermentation broth; the fermentation broth was centrifuged under the conditions of 4° C. and 12000 g for 10 min to obtain wet bacterial cells; the wet bacterial cells were crushed and then centrifuged under the conditions of 4° C. and 12000 g for 10 min, to obtain a cell disruption supernatant; and the enzyme activity of linoleic acid isomerase in the obtained cell disruption supernatant was detected. Detection results are as follows:

The enzyme activity of the linoleic acid isomerase in the cell disruption supernatant obtained by fermenting the *Lactobacillus plantarum* engineered strain *Lactobacillus plantarum* ST-III/pNZ44-bbi is 2.5 U/mg, and the enzyme activity of the linoleic acid isomerase in the cell disruption supernatant obtained by fermenting the *Lactobacillus plantarum* engineered strain *Lactobacillus plantarum* ST-III/pNZ44-bbi (U) is 10.5 U/mg. It can be seen that the *Lactobacillus plantarum* engineered strain *Lactobacillus plantarum* ST-III/pNZ44-bbi and the *Lactobacillus plantarum* engineered strain *Lactobacillus plantarum* ST-III/pNZ44-bbi (U) can successfully express the linoleic acid isomerase, but the expression ability of the *Lactobacillus plantarum* engineered strain *Lactobacillus plantarum* ST-III/pNZ44-bbi (U) is stronger.

TABLE 3

| Connecting System | | |
|---|---|---|
| Gene | Reagent | Dosage |
| bbi | 10 × reaction buffer | 2 μL |
|  | T4 ligase | 2 μL |
| bbi (U) | Template volume | 11.26 μg |
|  | Plasmid volume | 4.74 μL |
|  | 10 × reaction buffer | 2 μL |
|  | T4 ligase | 2 μL |
|  | Template volume | 10.26 μg |
|  | Plasmid volume | 5.74 μL |

Example 8. Application of *Lactobacillus plantarum* Engineered Strain

An MRS liquid culture medium containing 0.5 mg/mL free linoleic acid was inoculated with activated bacterial solutions of the obtained *Lactobacillus plantarum* engineered strain *Lactobacillus plantarum* ST-III/pNZ44-bbi and *Lactobacillus plantarum* engineered strain *Lactobacillus plantarum* ST-III/pNZ44-bbi (U) respectively according to the inoculation quantity of 1% (v/v) to be stationarily cultured at 37° C. for 72 h, so as to obtain fermentation broth; and a conversion rate of conjugated linoleic acid in the fermentation broth was detected, and types and ratios of conjugated linoleic acid isomers in the obtained conjugated linoleic acid were detected. See FIGS. 20-21 for detection results.

It can be known from the detection results that the fermentation broth obtained by fermenting the *Lactobacillus plantarum* engineered strain *Lactobacillus plantarum* ST-III/pNZ44-bbi does not contain the conjugated linoleic acid; and the conversion rate of the conjugated linoleic acid in the fermentation broth obtained by fermenting the *Lactobacillus plantarum* engineered strain *Lactobacillus plantarum* ST-III/pNZ44-bbi (U) can reach 89.9%.

Figure 20:
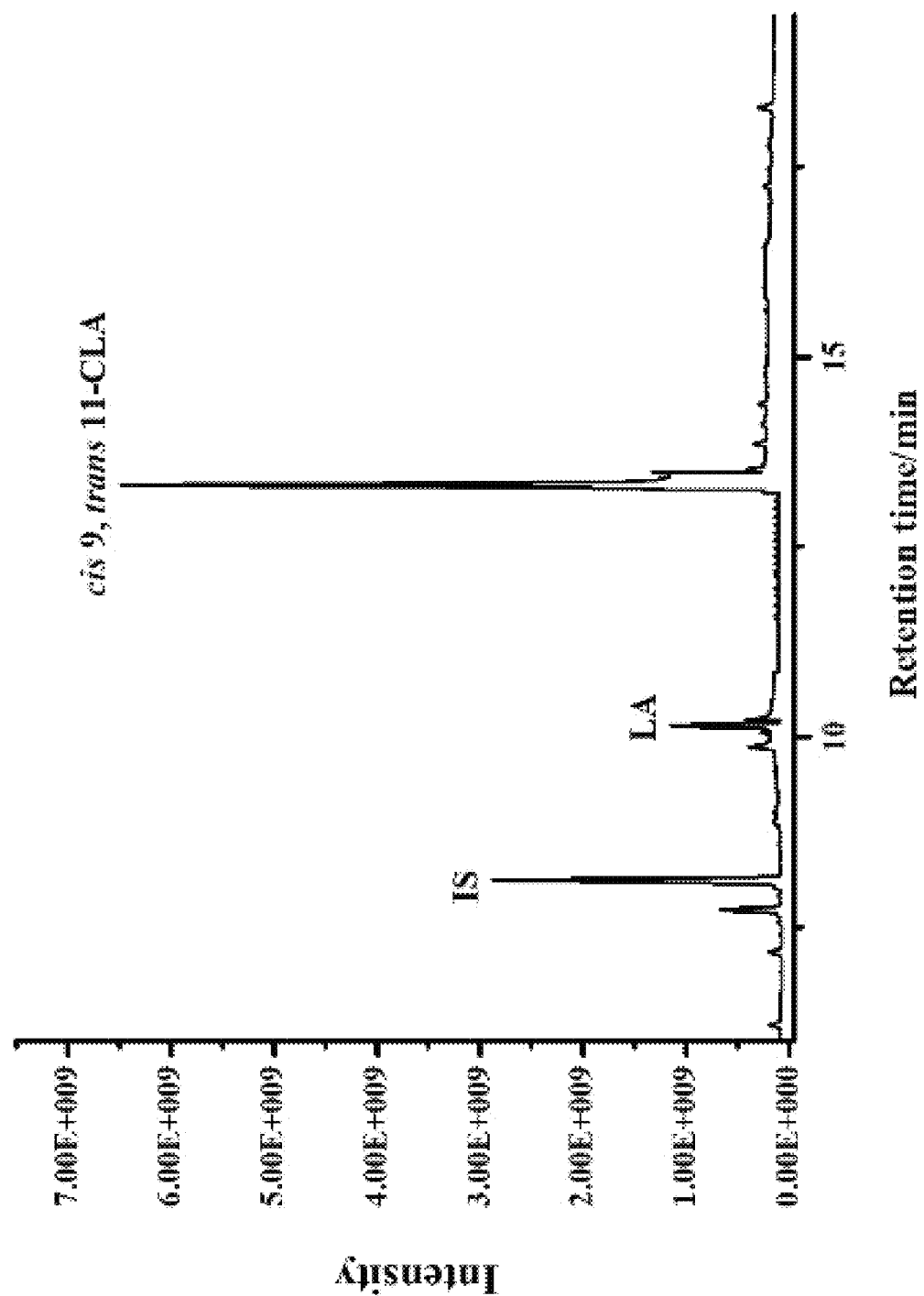
FIG. 20: A GC-MS identification chromatogram of conjugated linoleic acid produced by a Lactobacillus plantarum engineered strain Lactobacillus plantarum ST-III/pNZ44-bbi (U).
Figure 21:
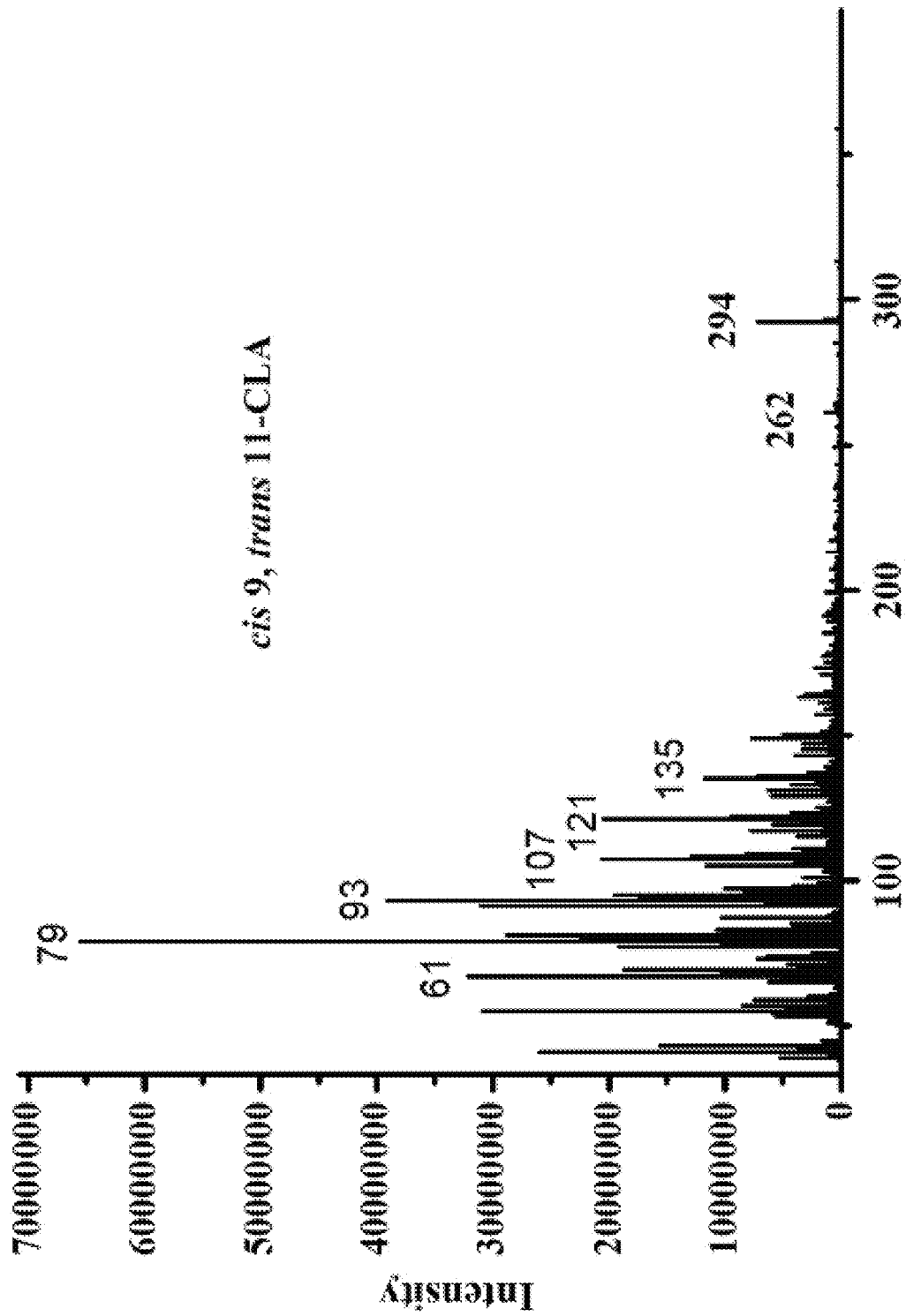
FIG. 21: A GC-MS mass fragmentography of conjugated linoleic acid produced by a Lactobacillus plantarum engineered strain Lactobacillus plantarum ST-III/pNZ44-bbi (U).

It can be known from FIGS. 20-21 that the conjugated linoleic acid obtained by fermenting the *Lactobacillus plantarum* engineered strain *Lactobacillus plantarum* ST-III/pNZ44-bbi (U) is cis9, trans11-CLA 100%.

What is claimed is:

1. A recombinant microbial cell, comprising a vector that contains a linoleic acid isomerase gene, wherein the linoleic acid isomerase gene comprises a nucleotide sequence set forth in SEQ ID NO: 5, 6, 7, 8, 17 or 18.

2. The recombinant cell of claim 1, wherein the recombinant cell is *E. coli, Yarrowia lipolytica* or *Lactobacillus plantarum*.

3. The recombinant cell of claim 2, wherein the recombinant cell is *E. coli*, the vector is pET-28a(+) plasmid, and the linoleic acid isomerase gene comprises a nucleotide sequence set forth in SEQ ID NO: 5, 6, 7 or 8; or wherein the recombinant cell is *Yarrowia lipolytica*, the vector is pINA 1312sp plasmid, and the linoleic acid isomerase gene comprises the nucleotide sequence set forth in SEQ ID NO: 17; or wherein the recombinant cell is *Lactobacillus planta-* *rum*, the vector is pNZ44 plasmid, and the linoleic acid isomerase gene comprises the nucleotide sequence set forth in SEQ ID NO: 18.

4. A method for producing conjugated linoleic acid using the recombinant cell of claim 1, comprising the steps of:
   a) culturing the recombinant cells in a culture medium;
   b) adding linoleic acid and/or glyceride during or after the culture of the recombinant cells to obtain a solution rich in conjugated linoleic acid; and
   c) extracting conjugated linoleic acid from the solution rich in conjugated linoleic acid.

5. The method of claim 4 using recombinant *E. coli* cells, comprising the steps of:
   a) culturing the recombinant *E. coli* cells at 35° C. to 40° C. with a rotating speed of 150 to 250 rpm until $OD_{600}$ is 0.4 to 0.6 to obtain a culture solution A;
   b) adding IPTG with a final concentration of 0.01 to 1.0 mM into the culture solution A;

c) performing induction culture at 15° C. to 20° C. with a rotating speed of 150 to 250 rpm for 12 to 16 h to obtain a culture solution B;

d) centrifuging the culture solution B and collecting wet bacterial cells;

e) adding the wet bacterial cells into a reaction system containing linoleic acid and performing reaction at 35° C. to 40° C. with a rotating speed of 150 to 250 rpm to obtain the solution rich in conjugated linoleic acid; and f) extracting conjugated linoleic acid from the solution rich in conjugated linoleic acid.

6. The method of claim 5, wherein the reaction system of step e) comprises a buffer solution and the linoleic acid.

7. The method of claim 6, wherein the buffer solution has a pH of 6 to 7.

8. The method of claim 5, wherein the linoleic acid in the reaction system has a concentration of 0.05 to 0.15 mg/mL.

9. The method of claim 5, wherein the wet bacterial cells in the reaction system has a concentration of 0.5 to 2 mg/mL.

10. The method of claim 4 using recombinant *Yarrowia lipolytica* cells, comprising the steps of:

a) culturing the recombinant *Yarrowia lipolytica* cells in a culture medium containing linoleic acid and/or glyceride at 35° C. to 40° C. with a rotating speed of 150 to 250 rpm to obtain the solution rich in conjugated linoleic acid; and b) extracting conjugated linoleic acid from the solution rich unconjugated linoleic acid.

11. The method of claim 10, wherein the glyceride is safflower oil, linseed oil, cottonseed oil, or soybean oil.

12. The method of claim 4 using recombinant *Lactobacillus plantarum* cells, comprising the steps of:

a) culturing the recombinant *Lactobacillus plantarum* cells in a culture medium containing linoleic acid at 37° C. to obtain the solution rich in conjugated linoleic acid; and b) extracting conjugated linoleic acid from the solution rich in conjugated linoleic acid.

13. The method of claim 4 using recombinant *E. coli* cells, comprising the steps of:

a) culturing the recombinant *E. coli* cells at 37° C. with a rotating speed of 200 rpm until $OD_{600}$ is 0.4 to 0.6 to obtain a culture solution A;

b) adding IPTG with a final concentration of 0.01 to 1.0 mM into the culture solution A;

c) performing induction culture at 18° C. with a rotating speed of 200 rpm for 12 to 16 h to obtain a culture solution B;

d) centrifuging the culture solution B and collecting wet bacterial cells;

e) adding the wet bacterial cells into a reaction system containing linoleic acid and performing reaction at 37° C. with a rotating speed of 200 rpm to obtain the solution rich in conjugated linoleic acid; and f) extracting conjugated linoleic acid from the solution rich unconjugated linoleic acid.

14. The method of claim 4, wherein the recombinant cell is *E. coli*, and the conjugated linoleic acid is cis9, trans11-CLA, and/or trans9, trans11-CLA; or wherein the recombinant cell is *Yarrowia lipolytica*, and the conjugated linoleic acid is cis9, trans11-CLA, trans10, cis12-CLA and/or trans9, trans11-CLA; or wherein the recombinant cell is *Lactobacillus plantarum* and the conjugated linoleic acid is cis9, trans11-CLA.

15. A method for producing linoleic acid isomerase using recombinant cells of claim 1, comprising:

a) culturing the recombinant cells in a culture medium to express the linoleic acid isomerase; and b) extracting the linoleic acid isomerase from the recombinant cells, wherein the recombinant cells are selected from *E. coli, Yarrowia lipolytica* or *Lactobacillus plantarum*.

16. The method of claim 15, comprising:

a) culturing the recombinant cells at 35° C. to 40° C. with a rotating speed of 150 to 250 rpm to obtain recombinant cells rich in linoleic acid isomerase, wherein the recombinant cells are *E. coli* or *Yarrowia lipolytica*; and b) extracting linoleic acid isomerase from the recombinant cells rich in linoleic acid isomerase.

17. The method of claim 15, comprising:

a) culturing the recombinant *Lactobacillus plantarum* cells at 37° C. to obtain recombinant cells rich in linoleic acid isomerase; and b) extracting linoleic acid isomerase from the recombinant cells rich in linoleic acid isomerase.

18. The method of claim 15, wherein the recombinant cell is *E. coli* and the culture medium is an LB culture medium; or wherein the recombinant cell is *Yarrowia lipolytica* and the culture medium is a YPD culture medium; or where the recombinant cell is *Lactobacillus plantarum* and the culture medium is an MRS culture medium.

* * * * *